US009150593B2

(12) United States Patent
Cook et al.

(10) Patent No.: US 9,150,593 B2
(45) Date of Patent: *Oct. 6, 2015

(54) FLUOROERGOLINE ANALOGS

(71) Applicant: MAP Pharmaceuticals, Inc., Irvine, CA (US)

(72) Inventors: Robert O. Cook, Hillsborough, NJ (US); Jian Zhang, Mountain View, CA (US); Thomas A. Armer, Mountain View, CA (US)

(73) Assignee: MAP Pharmaceuticals, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/568,598

(22) Filed: Dec. 12, 2014

(65) Prior Publication Data

US 2015/0099755 A1    Apr. 9, 2015

Related U.S. Application Data

(63) Continuation of application No. 14/047,839, filed on Oct. 7, 2013, now Pat. No. 8,933,093, which is a continuation of application No. 13/531,371, filed on Jun. 22, 2012, now Pat. No. 8,604,035.

(60) Provisional application No. 61/571,299, filed on Jun. 23, 2011.

(51) Int. Cl.
| | | |
|---|---|---|
| *A61K 31/495* | (2006.01) | |
| *C07D 519/00* | (2006.01) | |
| *C07D 519/02* | (2006.01) | |
| *C07D 498/14* | (2006.01) | |
| *A61K 9/00* | (2006.01) | |
| *A61K 31/4985* | (2006.01) | |
| *C07D 457/04* | (2006.01) | |
| *C07D 498/04* | (2006.01) | |

(52) U.S. Cl.
CPC ............ *C07D 519/00* (2013.01); *A61K 9/0075* (2013.01); *A61K 9/0078* (2013.01); *A61K 31/4985* (2013.01); *C07D 498/14* (2013.01); *C07D 519/02* (2013.01); *A61K 31/495* (2013.01); *C07D 457/04* (2013.01); *C07D 498/04* (2013.01)

(58) Field of Classification Search
CPC .. C07D 457/10; C07D 457/04; C07D 498/04; A61K 31/498; A61K 31/4738; A61K 31/495
See application file for complete search history.

(56) References Cited

U.S. PATENT DOCUMENTS

| | | | |
|---|---|---|---|
| 2,886,568 A | 5/1959 | Stansbury, Jr. et al. | |
| 3,113,133 A | 12/1963 | Hofmann et al. | |
| 3,190,884 A | 6/1965 | Hofmann et al. | |
| 3,218,324 A | 11/1965 | Hofmann et al. | |
| 3,336,311 A | 8/1967 | Hofmann et al. | |
| 3,536,809 A | 10/1970 | Applezweig | |
| 3,586,683 A | 6/1971 | Sadler et al. | |
| 3,598,123 A | 8/1971 | Zaffaroni | |
| 3,652,569 A | 3/1972 | Stadler et al. | |
| 3,666,762 A | 5/1972 | Guttmann et al. | |
| 3,681,355 A | 8/1972 | Guttmann et al. | |
| 3,710,795 A | 1/1973 | Higuchi et al. | |
| 3,755,328 A | 8/1973 | Sadler et al. | |
| 3,814,765 A | 6/1974 | Bernardi et al. | |
| 3,845,770 A | 11/1974 | Theeuwes et al. | |
| 3,916,899 A | 11/1975 | Theeuwes et al. | |
| 3,922,347 A | 11/1975 | Bach et al. | |
| RE28,819 E | 5/1976 | Thompson | |
| 4,005,089 A | 1/1977 | Mago et al. | |
| 4,008,719 A | 2/1977 | Theeuwes et al. | |
| 4,044,126 A | 8/1977 | Cook et al. | |
| 4,124,712 A | 11/1978 | Stutz et al. | |
| 4,165,376 A | 8/1979 | Rosenberg | |

(Continued)

FOREIGN PATENT DOCUMENTS

| | | |
|---|---|---|
| CH | 610330 | 4/1979 |
| DE | 3700825 A1 | 7/1987 |

(Continued)

OTHER PUBLICATIONS

Supplementary European Search Report mailed on Jan. 19, 2015, for PCT/US2012/043677, 6 Pages.
Newman-Tancredi, Differential Actions of Antiparkinson Agents at Multiple Classes of Monoaminergic Receptor.II. Agonist and Antagonist Properties at Subtypes of Dopamine D2-Like Receptor and a1/a2-Adrenoceptor, J Pharmacology and Experimental Therapies 303(2):805-814, 2002.
Guillory, K. Chapter 5, pp. 202-205 in Polymorphism in Pharmaceutical Solids, (Brittain, H. ed.), Marcel Dekker, Inc., New York, NY, 1999.
Brittain, H., Chapter 6, pp. 227-278 in Polymorphism in Pharmaceutical Solids, (Brittain, H. ed.), Marcel Dekker, Inc. New York, 1999.
Guillory, K., Chapter 5, pp. 205-208 in Polymorphism in Pharmaceutical Solids, (Brittain, H. ed.), Marcel Dekker, Inc., New York, NY, 1999.
Carstensen, Jens T., Drug Stability: Principles & Practice, 2d. Ed., Marcel Dekker, NY, NY, 1995, pp. 379-380.

(Continued)

*Primary Examiner* — Alexander R Pagano
(74) *Attorney, Agent, or Firm* — Barbara C. Potts

(57) ABSTRACT

Provided herein are novel fluoroergoline derivatives and compositions thereof. In other embodiments, provided herein are methods of treatment, prevention, or amelioration of a variety of medical disorders such as, for example, migraine using the compounds and compositions disclosed herein. In still other embodiments, provided herein are methods of agonizing receptors such as, for example, the $5\text{-}HT_{1D}$ and/or the $5\text{-}HT_{1B}$ receptor, without agonizing the $5\text{-}HT_{2B}$ receptor using the compounds and compositions disclosed herein. In still other embodiments, provided herein are methods of antagonizing or inhibiting activity at receptors such as, for example, the adrenergic $alpha_{2A}$ and/or the $alpha_{2B}$ receptors using the compounds and compositions disclosed herein.

11 Claims, 4 Drawing Sheets

(56) References Cited

U.S. PATENT DOCUMENTS

| | | |
|---|---|---|
| 4,230,854 A * | 10/1980 | Beacco et al. ............... 544/346 |
| 4,328,245 A | 5/1982 | Yu |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu |
| 4,414,209 A | 11/1983 | Cook et al. |
| 4,522,811 A | 6/1985 | Eppstein et al. |
| 4,547,500 A | 10/1985 | Bolliger et al. |
| 4,675,404 A | 6/1987 | Bernardi et al. |
| 4,804,660 A | 2/1989 | Kobel et al. |
| 5,033,252 A | 7/1991 | Carter |
| 5,052,558 A | 10/1991 | Carter |
| 5,059,595 A | 10/1991 | LeGrazie |
| 5,073,543 A | 12/1991 | Marshall et al. |
| 5,120,548 A | 6/1992 | McClelland et al. |
| 5,158,957 A | 10/1992 | Brumby et al. |
| 5,323,907 A | 6/1994 | Kalvelage |
| 5,354,556 A | 10/1994 | Sparks et al. |
| 5,401,748 A | 3/1995 | Sauer et al. |
| 5,591,767 A | 1/1997 | Mohr et al. |
| 5,639,476 A | 6/1997 | Oshlack et al. |
| 5,639,480 A | 6/1997 | Bodmer et al. |
| 5,668,155 A | 9/1997 | Cincotta et al. |
| 5,674,533 A | 10/1997 | Santus et al. |
| 5,705,510 A | 1/1998 | DeSantis et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,860,957 A | 1/1999 | Jacobsen et al. |
| 5,877,183 A | 3/1999 | Cincotta |
| 5,891,474 A | 4/1999 | Busetti et al. |
| 5,900,252 A | 5/1999 | Calanchi et al. |
| 5,922,356 A | 7/1999 | Koseki et al. |
| 5,948,433 A | 9/1999 | Burton et al. |
| 5,972,366 A | 10/1999 | Haynes et al. |
| 5,972,891 A | 10/1999 | Kamei et al. |
| 5,980,945 A | 11/1999 | Ruiz |
| 5,983,134 A | 11/1999 | Ostrow |
| 5,985,307 A | 11/1999 | Hanson et al. |
| 5,985,317 A | 11/1999 | Venkateshwaran et al. |
| 5,993,855 A | 11/1999 | Yoshimoto et al. |
| 6,004,534 A | 12/1999 | Langer et al. |
| 6,010,715 A | 1/2000 | Wick et al. |
| 6,024,975 A | 2/2000 | D'Angelo et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,167,301 A | 12/2000 | Flower et al. |
| 6,197,350 B1 | 3/2001 | Yamagata et al. |
| 6,221,870 B1 | 4/2001 | Pfaeffli et al. |
| 6,248,363 B1 | 6/2001 | Patel et al. |
| 6,253,872 B1 | 7/2001 | Neumann |
| 6,256,533 B1 | 7/2001 | Yuzhakov et al. |
| 6,261,595 B1 | 7/2001 | Stanley et al. |
| 6,264,970 B1 | 7/2001 | Hata et al. |
| 6,267,981 B1 | 7/2001 | Okamoto et al. |
| 6,267,983 B1 | 7/2001 | Fujii et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada et al. |
| 6,740,634 B1 | 5/2004 | Saikawa et al. |
| 6,855,707 B2 | 2/2005 | Cincotta |
| 7,217,822 B2 | 5/2007 | Comin et al. |
| 7,666,877 B2 | 2/2010 | Baenteli et al. |
| 8,178,529 B2 | 5/2012 | Arvidsson et al. |
| 8,592,445 B2 * | 11/2013 | Zhang et al. ............... 514/288 |
| 8,604,035 B2 * | 12/2013 | Cook et al. ............... 514/250 |
| 8,710,092 B2 * | 4/2014 | Zhang et al. ............... 514/410 |
| 8,722,699 B2 * | 5/2014 | Zhang et al. ............... 514/288 |
| 8,841,448 B2 * | 9/2014 | Cook et al. ............... 544/346 |
| 8,927,567 B2 * | 1/2015 | Cook et al. ............... 514/288 |
| 8,933,093 B2 * | 1/2015 | Cook et al. ............... 514/288 |
| 8,946,420 B2 * | 2/2015 | Cook et al. ............... 546/68 |
| 8,969,374 B2 * | 3/2015 | Zhang et al. ............... 514/288 |
| 9,012,640 B2 * | 4/2015 | Zhang et al. ............... 546/69 |
| 2007/0020299 A1 | 1/2007 | Pipkin et al. |
| 2007/0225312 A1 | 9/2007 | Ludwig et al. |
| 2009/0264456 A1 | 10/2009 | Sewell et al. |
| 2010/0048587 A1 | 2/2010 | Cook et al. |
| 2010/0081663 A1 | 4/2010 | Cook et al. |
| 2010/0226943 A1 | 9/2010 | Brennan et al. |
| 2011/0152280 A1 * | 6/2011 | Cook et al. ............... 514/250 |
| 2012/0329806 A1 * | 12/2012 | Cook et al. ............... 514/250 |
| 2013/0158064 A1 | 6/2013 | Zhang et al. ............... 514/288 |
| 2013/0165469 A1 * | 6/2013 | Cook et al. ............... 514/288 |
| 2013/0345253 A1 * | 12/2013 | Zhang et al. ............... 514/288 |
| 2014/0039188 A1 * | 2/2014 | Zhang et al. ............... 544/346 |
| 2014/0066450 A1 * | 3/2014 | Cook et al. ............... 514/250 |
| 2014/0073647 A1 * | 3/2014 | Cook et al. ............... 514/250 |
| 2014/0073790 A1 * | 3/2014 | Cook et al. ............... 544/346 |
| 2014/0094483 A1 * | 4/2014 | Zhang et al. ............... 514/288 |
| 2014/0179706 A1 * | 6/2014 | Armer et al. ............... 514/250 |
| 2014/0179707 A1 * | 6/2014 | Armer et al. ............... 514/250 |
| 2014/0194434 A1 * | 7/2014 | Cook et al. ............... 514/250 |
| 2014/0194435 A1 * | 7/2014 | Cook et al. ............... 514/250 |
| 2015/0023888 A1 * | 1/2015 | Cook et al. ............... 424/45 |

FOREIGN PATENT DOCUMENTS

| | | |
|---|---|---|
| EP | 0296748 | 4/1993 |
| GB | 1485738 A | 9/1977 |
| WO | WO9746239 | 12/1997 |
| WO | WO02-49608 A1 | 6/2002 |
| WO | WO2005-025506 A2 | 3/2005 |
| WO | WO2005-025506 A3 | 3/2006 |
| WO | WO2011-079313 A1 | 6/2011 |
| WO | WO2012-177962 A1 | 12/2012 |

OTHER PUBLICATIONS

Slassi et al., 5-Alkyltryptamine Derivatives as Highly Selective and Potent 5-HT1D Receptor Agonists, Bioorg. Med. Chem. Lett. 10: 1707-1709 (2000).

Castro, et al., Enhancement of Oral Absorption in Selective 5-HT1D Receptor Agonists: Fluorinated 3-[3-(Piperidin-1-yl)propyl]indoles, J. Med. Chem. 41: 2667-2670 (1998).

Ennis, et al., Isochroman-6-carboxamides as Highly Selective 5-HT1D Agonists: Potential New Treatment for Migraine without Cardiovascular Side Effects, J. Med. Chem.41:2180-2183 (1998).

Phebus, Cephalalgia 17: 245 (1997). Abstract Only.

Rothman, et al., Evidence for Possible Involvement of 5-HT2B Receptors in the Cardiac Valvulopathy Associated with Fenfluramine and other Serotonergic Medications, Circulation 102: 2836-2841 (2000).

Schaerlinger, et al., Agonist actions of dihydroergotamine at 5-HT2B and 5-HT2C receptors and their possible relevance to antimigraine efficacy, Br. J.Pharmacol. 140(2): 277-84, (2003).

Kalani, et al. The Predicted 3D structure of the human D2 dopamine receptor and the binding site and binding affinities for agaonists and antagonists. PNAS, 2004, vol. 101(11), pp. 3815-3820, p. 3816, col. 2, para 2-p. 3819, col. 2, para 3. Downloaded at www.pnas.org/content/101/11/3815.long.

Jordan, V.C. Tamoxifen: A Most Unlikely Pioneering Medicine, Nature Reviews: Drug Discovery, 2, 2003, 205-213.

Vippagunta, et al. Crystalline solids, Advanced Drug Delivery Reviews, 48, 2001, 4-26.

Fluckiger, et al. Ergot Compounds and Prolactin Secretion, Developments in Endocrinology (Amsterdam), 2, 1978, 383-396.

(56) References Cited

OTHER PUBLICATIONS

Aellig, W.H., et al., Studies of the effect of natural and synthetic polypeptide type ergot compounds on a peripheral vascular bed, Brit. J. Pharmacol., 1969, 36(3):561-570.
Beran, M. et al., 9 10-Dihydroergopeptines Modified in Position 6, Ergot Alkaloids. LXXIII. 9,10-Dihydroergopeptines Modified in Position 6, Collect. Czech. Chem. Commun, 1990, 55(3):819-832.
Buchwald, H. et al., Long-Term, continuous Intravenous Heparin Administration by an Implantable Infusion Pump in Ambulatory Patients with Recurrent Venous Thrombosis, Surgery, 1980, 88(4): 507-516.
Goernemann, T., et al. Pharmacological Properties of a Wide Array of Ergolines at Functional Alpha1-Adrenoceptor Subtypes, Naunyn-Schmiedeberg's Arch. Pharmacol., 2008, 376(5): 321-330.
Goodson, J.M., Dental Applications, Medical Applications of Controlled Release, vol. II, Chapter 6, pp. 115-138, CRC Press, Inc., Boca Raton, FL, 1984.
International Search Report and Written Opinion mailed Mar. 20, 2011, for PCT/US2010/62098.
Langer, R., New Methods of Drug Delivery, Science, 1990, 249(4976):1527-1532.
Saudek, C.D., et al., A Preliminary Trial of the Programmable Implantable Medication System for Insulin Delivery, N. Eng.J.Med., 1989, 321:574-579.
Schreier, E., Ergot Alkaloids. 83. Radiolabeled Peptide Ergot Alkaloids, Helvetica Chimica Acta, 1976, 59(2): 585-606.
Sefton, M.V., Implantable Pumps, Crit. Rev. Biomed, Eng., 1987, 14(3):201-240.
Weber, H.P., The Molecular Architecture of Ergopeptines: a Basis for Biological Interaction, Adv. Biochem. Psychopharmacol., 1980, 25-34.
Restriction Requirement dated Nov. 14, 2011, and Response to Restriction Requirement as filed Dec. 14, 2011, for U.S. Appl. No. 12/978,314, 22 pages.
Non-Final Office Action dated Jan. 25, 2012, and Response to Non-Final Office Action as filed Apr. 25, 2012, for U.S. Appl. No. 12/978,314, 40 pages.
Final Rejection dated May 2, 2012, and Notice of Appeal as filed Aug. 2, 2012, for U.S. Appl. No. 12/978,314, 20 pages.
Egan, et al. Agonist Activity of LSD and lisuride at cloned 5HT2A and 5HTC receptors, Psychopharmacology (1998) 136:409-414.
International Search Report and Written Opinion mailed Aug. 28, 2012, for PCT/US2012/043687.
International Search Report and Written Opinion mailed Sep. 12, 2012, for PCT/US2012/043686.
International Search Report and Written Opinion mailed Sep. 12, 2012, for PCT/US2012/043677.
RCE & Amendment as filed Feb. 4, 2013, for U.S. Appl. No. 12/978,314, 34 pages.
Non-Final Office Action dated Apr. 1, 2013, for U.S. Appl. No. 12/978,314, 17 pages.
Hofmann, et al. Fast estimation of crystal densities, Acta Crystallographica B57: 489-493 (2002).
Marini, et al. Physico-Chemical Characterization of Drugs and Drug Forms in the Solid State, Curr. Med. Chem 2(4): 303-321 (2003).
McClurg, et al. X-ray Powder Diffraction Pattern Indexing for Pharmaceutical Applications, Pharm. Tech. Europe, http://www.pharmtech.com/pharmtech/Peer-Reviewed+Research/X-ray-Powder-Diffraction-Pattern-Indexing-for-Phar/ArticleStandard/Article/detail/800851, 7 pgs. (Jan. 2013).
Cook, et al. Reduced Adverse Event Profile of Orally Inhaled DHE (MAP0004) vs IV DHE: Potential Mechanism, Headache 49(10): 1423-1434 (2009).
Silberstein, et al. Ergotamine and Dihydroergotamine: History, Pharmacology, and Efficacy, Headache 43(2): 144-166 (2003).
Notice of Allowance dated Aug. 22, 2013, for U.S. Appl. No. 13/531,371, filed Jun. 22, 2012.
Amendment after Notice of Allowance filed Oct. 3, 2013, for U.S. Appl. No. 13/531,371, filed Jun. 22, 2012.
U.S. Appl. No. 12/978,314.
U.S. Appl. No. 13/531,416, filed Jun. 22, 2012.
Purser, et al., Fluorine in Medicinal Chemistry,Chemical Society Reviews, vol. 37, No. 2, Feb. 1, 2009, pp. 320-330.

\* cited by examiner

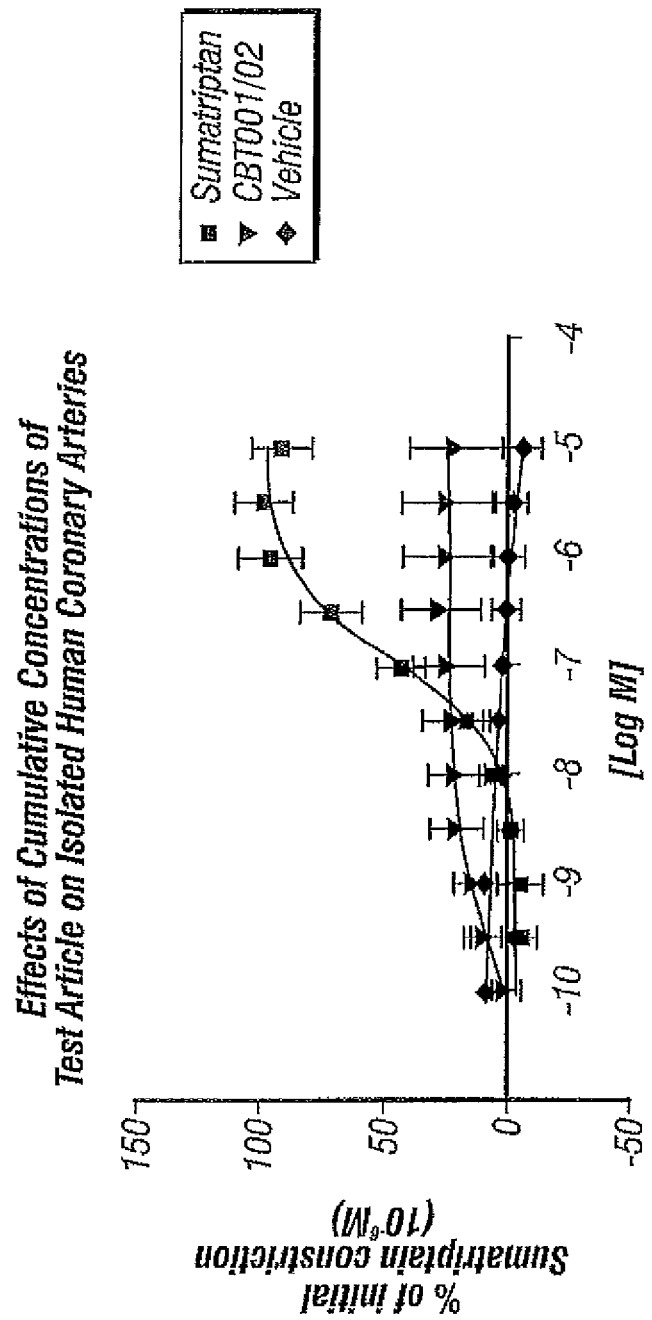

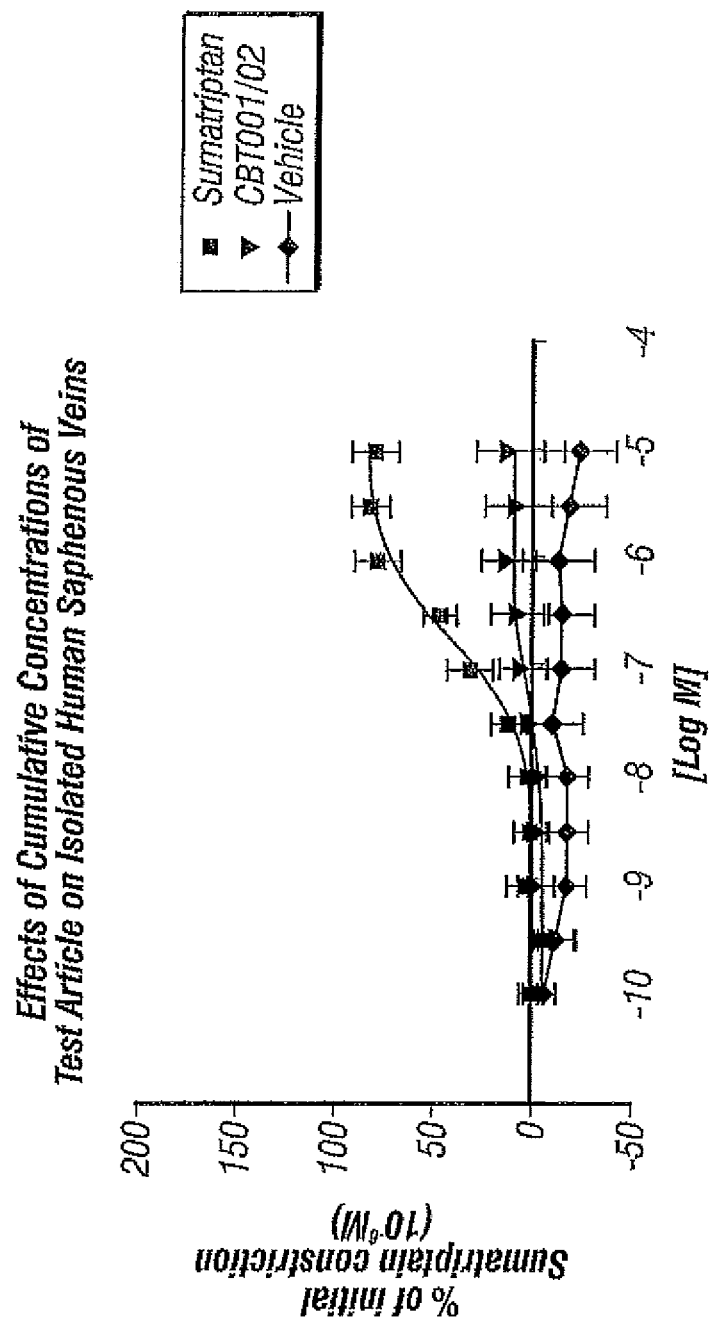

FLUOROERGOLINE ANALOGS

This application is a continuation of U.S. patent application Ser. No. 14/047,839, filed on Oct. 7, 2013, which is a continuation of U.S. patent application Ser. No. 13/531,371, filed on Jun. 22, 2012, which claims priority under 35 U.S.C. §119(e) from U.S. Provisional Application Ser. No. 61/571,299, filed on Jun. 23, 2011, which are hereby incorporated by reference in their entirety.

FIELD

Provided herein are novel fluoroergoline derivatives and compositions thereof. In other embodiments, provided herein are methods of treatment, prevention, or amelioration of a variety of medical disorders such as, for example, migraine using the compounds and compositions disclosed herein. In still other embodiments, provided herein are methods of agonizing receptors such as, for example, the 5-$HT_{1D}$ and/or the 5-$HT_{1B}$ receptor, without agonizing the 5-$HT_{2B}$ receptor using the compounds and compositions disclosed herein. In still other embodiments, provided herein are methods of antagonizing or inhibiting activity at receptors such as, for example, the adrenergic alpha$_{2A}$ and/or the alpha$_{2B}$ receptors using the compounds and compositions disclosed herein.

BACKGROUND

Ergotamines such as, for example, dihydroergotamine mesylate are well established therapeutic agents for the treatment of migraine. More recently, a number of highly selective agents for the treatment of migraine which have high 5-$HT_{1D}$: 5-$HT_{1B}$ binding ratios have been prepared, such as, for example, the alkyltryptamine derivatives (125-fold selectivity, Slassi, *Bioorg. Med. Chem. Lett.* 10: 1707-1709, (2000)), the indole series (300-fold selectivity, Castro, *J. Med. Chem.* 41: 2667 (1998)) and from the non-indole series (>6000 fold selectivity, Ennis, *J. Med. Chem.* 41: 2180 (1998)). However, strong agonism of 5-$HT_{1B}$ by migraine therapeutics such as, for example, sumatriptan (Phebus, *Cephalalgia* 17: 245 (1997)) frequently leads to adverse cardiovascular effects due to excessive vasoconstriction. Accordingly, an effective migraine agent should be selective for the 5-$HT_{1D}$ receptor over the 5-$HT_{1B}$ receptor, but with moderate agonism of the 5-$HT_{1B}$ receptor to minimize non-cranial vasoconstriction. Antagonism of adrenergic receptors, such as, for example, alpha$_{1A}$, alpha$_{1D}$, alpha$_{2A}$, alpha$_{2B}$ and alpha$_{2C}$ by migraine therapeutics can reduce vasoconstriction caused by strong 5-$HT_{1B}$ agonism.

Agonism of dopamine receptors is highly unfavorable for anti-migraine compounds since nausea is a classic dopaminergic (activation of dopamine receptors) symptom, which is already an indication of migraine itself. Yet another problem with many migraine therapeutics and especially ergoline derivatives is undesirable agonism of 5-$HT_{2B}$ receptors which is associated with cardiac and non-cardiac fibrosis, including cardiovascular valvulopathy (Rothman, *Circulation* 102: 2836 (2000)). Conversely, antagonism of 5-$HT_{2B}$ receptors may offer therapeutic advantages in the treatment and/or prevention of migraine (Schaerlinger, *Br. J. Pharmacol.* 140(2): 277-84, (2003)).

Accordingly, there is a continuing need for less toxic ergoline derivatives to treat and/or prevent disorders such as, for example, migraine, which selectively agonize 5-$HT_{1D}$ receptors over 5-$HT_{1B}$ receptors with moderated 5-$HT_{1B}$ receptor agonism, have low dopamine receptor agonism and are 5-$HT_{2B}$ and adrenergic receptor antagonists.

SUMMARY

Provided herein are fluoroergoline derivatives which address these and other needs. In one aspect, the fluoroergoline derivatives described herein include compounds of Formula (I) or (II):

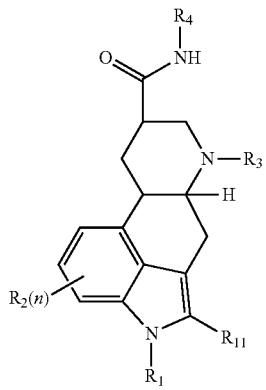

(I)

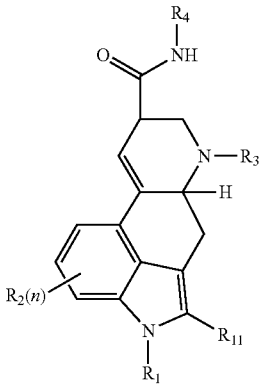

(II)

or ion pairs, polymorphs, salts, hydrates or solvates thereof, wherein:

$R_1$ is hydrogen, ($C_1$-$C_4$) alkyl, substituted ($C_1$-$C_4$) alkyl or ($C_1$-$C_4$) alkyl substituted with one or more fluorine atoms;

$R_2$ is alkyl, substituted alkyl, acyl, substituted acyl, halo, heteroalkyl, substituted heteroalkyl, —$NO_2$, —$N_3$, —OH, —S(O)$_k$$R_{100}$, —O$R_{101}$, —N$R_{102}$$R_{103}$, —CON$R_{104}$$R_{105}$, —$CO_2$$R_{106}$ or —$O_2$C$R_{107}$;

$R_3$ is hydrogen, ($C_1$-$C_3$) alkyl, ($C_1$-$C_3$) substituted alkyl or ($C_1$-$C_3$) alkyl substituted with one or more fluorine atoms;

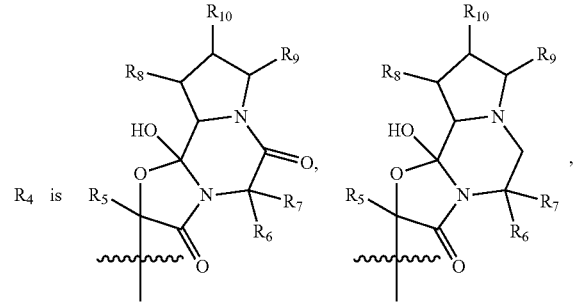

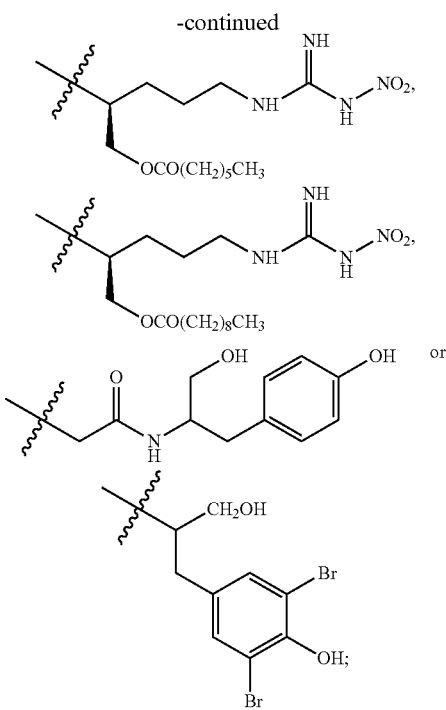

$R_5$ is ($C_1$-$C_4$) alkyl or ($C_1$-$C_4$) substituted alkyl;

$R_6$ is hydrogen, ($C_1$-$C_4$) alkyl, substituted ($C_1$-$C_4$) alkyl, benzyl or substituted benzyl;

$R_7$ is ($C_1$-$C_4$) alkyl, substituted ($C_1$-$C_4$) alkyl, benzyl or substituted benzyl;

$R_8$ is hydrogen, OH, =O, ($C_1$-$C_4$) alkyl, ($C_1$-$C_4$) substituted alkyl, —$CO_2R_{108}$ or —$CONR_{109}R_{110}$;

$R_9$ is hydrogen, OH, =O, ($C_1$-$C_4$) alkyl, ($C_1$-$C_4$) substituted alkyl, —$CO_2R_{111}$ or —$CONR_{112}R_{113}$;

$R_{10}$ is hydrogen, OH, =O, ($C_1$-$C_4$) alkyl, ($C_1$-$C_4$) substituted alkyl, —$CO_2R_{114}$ or —$CONR_{115}R_{116}$;

$R_{11}$ is ($C_1$-$C_3$) alkyl substituted with one or more fluorine atoms;

$R_{100}$-$R_{116}$ are independently hydrogen, alkyl, substituted alkyl, acyl, substituted acyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

k is 0, 1 or 2; and n is 0, 1, 2 or 3.

Also provided are derivatives, including salts, esters, enol ethers, enol esters, solvates, hydrates and prodrugs of the compounds described herein. Further provided are compositions which include the compounds provided herein and a vehicle.

Methods of treating, preventing, or ameliorating symptoms of medical disorders such as, for example, migraine, ALS, Parkinson's disease, extra-pyramidal disorders, depression, nausea, restless legs syndrome, insomnia, aggression, Huntington's disease, dystonia, parsomnia and hyperlactinemia are also provided herein. In practicing the methods, therapeutically effective amounts of the compounds or compositions thereof are administered to a subject.

Methods of antagonizing receptors such as, for example 5-$HT_{2B}$, adrenergic receptors such as, for example, alpha$_{1A}$, alpha$_{1D}$, alpha$_{2A}$, alpha$_{2B}$ and alpha$_{2C}$ with the compounds and compositions described herein are also provided herein. In practicing the methods, therapeutically effective amounts of the compounds or compositions are administered.

Methods of agonizing receptors such as, for example, 5-$HT_{1D}$ and 5-$HT_{1B}$, receptors with the compounds and compositions described herein are also provided herein. In some embodiments, methods of selectively agonizing the 5-$HT_{1D}$ receptor over the 5-$HT_{1B}$ receptor are provided. In other embodiments, methods of reducing agonism of dopamine receptors when compared to agonism of dopamine receptors by other ergolines, such as, for example, dihydroergotamine, an existing anti-migraine agent, with the compounds and compositions described herein are also provided herein. In practicing the methods, therapeutically effective amounts of the compounds or compositions are administered.

DESCRIPTION OF THE FIGURES

FIG. 5 illustrates that 2-CF3-DHE (CBT001/02) displayed a slight mean increase in tension as compared to positive control, sumatriptan (both at concentrations from 100 pM to 10 μM) when tested in constriction assays using human coronary arteries (n=6 for each condition).

FIG. 6 illustrates that 2-CF3-DHE (CBT001/02) displayed no change in tension as compared to positive control, sumatriptan (both at concentrations from 100 pM to 10 10 μM) when tested in constriction assays using human saphenous veins (n=6 for each condition).

DETAILED DESCRIPTION

Definitions

Figure 1:
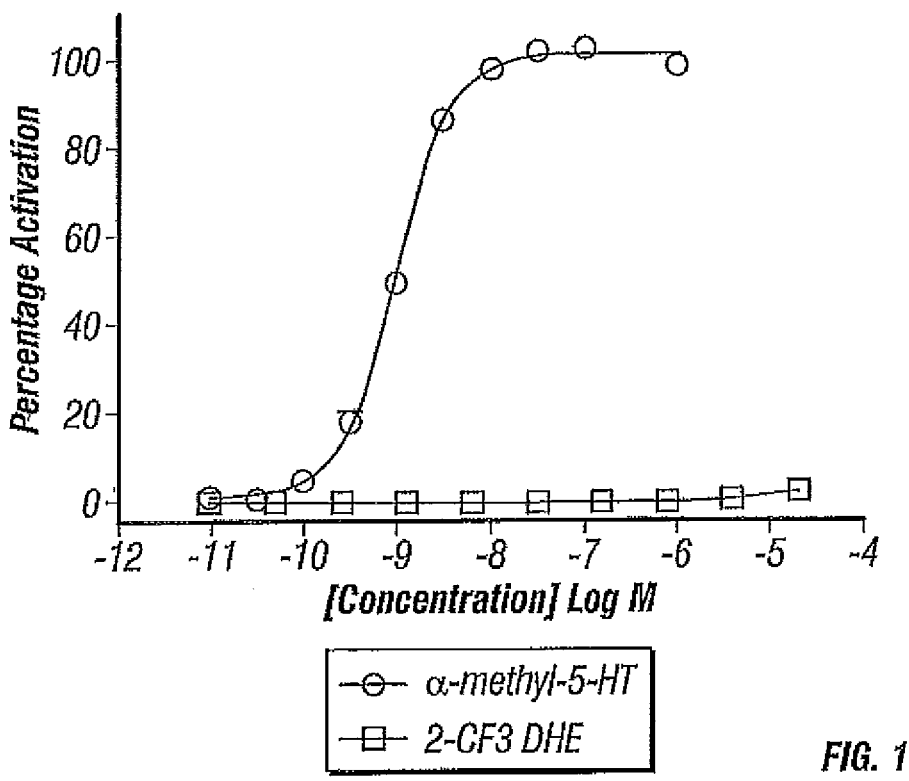
FIG. 1 illustrates that 2-$CF_3$-dihydroergotamine has little agonist activity against the 5-$HT_{2B}$ receptor.

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)$R^{400}$, where $R^{400}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Compounds" refers to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds described herein include, but are not limited to, $^2$H, $^3$H, $^{13}$C, $^{14}$C, $^{15}$N, $^{18}$O, $^{17}$O, $^{35}$S, etc. In general, it should be understood that all isotopes of any of the elements comprising the compounds described herein may be found in these compounds. Compounds may exist in unsolvated or unhydrated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$—, =N—N=, —N=N—, —N=N—NR$^{503}$R$^{404}$, —PR$^{505}$—, —P(O)$_2$—, —POR$^{506}$—, —O—P(O)$_2$—, —SO—, —SO$_2$, —SnR$^{507}$R$^{508}$— and the like, where R$^{501}$, R$^{502}$, R$^{503}$, R$^{504}$, R$^{505}$, R$^{506}$, R$^{507}$ and R$^{508}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is (C$_1$-C$_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is (C$_1$-C$_3$) alkyl and the heteroaryl moiety is a 5-10 membered heteroaryl.

"Hydrates" refers to incorporation of water into to the crystal lattice of a compound described herein, in stochiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202-205 in *Polymorphism in Pharmaceutical Solids*, (Brittain, H. ed.), Marcel Dekker, Inc., New York, N.Y., 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-Ray diffraction, X-Ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymorphism in Pharmaceutical Solids*, (Brittain, H. ed.), Marcel Dekker, Inc. New York, 1999). In addition, many commercial companies routine offer services that include preparation and/or characterization of hydrates such as, for example, HOLODIAG, Pharmaparc II, Voie de l'Innovation, 27 100 Val de Reuil, France (http://www.holodiag.com).

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, B, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by taking the compound in a preventative fashion. The application of a therapeutic for preventing or prevention of a disease of disorder is known as 'prophylaxis.' In some embodiments, the compounds provided herein provide superior prophylaxis because of lower long term side effects over long time periods.

"Prodrug" refers to a derivative of a drug molecule that requires a transformation within the body to release the active drug. Prodrugs are frequently (though not necessarily) pharmacologically inactive until converted to the parent drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. In some embodiments, the salt is pharmaceutically acceptable.

"Solvates" refers to incorporation of solvents into to the crystal lattice of a compound described herein, in stochiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion, etc. Solvates may also be formed, under certain circumstances, from other crystalline solvates or hydrates upon exposure to the solvent or upon suspension material in solvent. Solvates may crystallize in more than one form resulting in solvate polymorphism. See e.g., (Guillory, K., Chapter 5, pp. 205-208 in *Polymorphism in Pharmaceutical Solids*, (Brittain, H. ed.), Marcel Dekker, Inc. New York, N.Y., 1999)). The above methods for preparing solvates are well within the ambit of those of skill in the art, are completely conventional do not require any experimentation beyond what is typical in the art. Solvates may be characterized and/or analyzed by methods well known to those of skill in the art such as, for example, single crystal X-Ray diffraction, X-Ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymorphism in Pharmaceutical Solids*, (Brittain, H. ed.), Marcel Dekker, Inc. New York, 1999). In addition, many commercial companies routine offer services that include preparation and/or characterization of solvates such as, for example, HOLODIAG, Pharmaparc II, Voie de l'Innovation, 27 100 Val de Reuil, France (http://www.holodiag.com).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art. The substituents used to substitute a specified group can be further substituted, typically with one or more of the same or different groups selected from the various groups specified above. In some embodiments, substituents are limited to the groups above.

"Subject," "individual" or "patient" is used interchangeably herein and refers to a vertebrate, preferably a mammal. Mammals include, but are not limited to, murines, rodents, simians, humans, farm animals, sport animals and pets.

"Treating" or "treatment" of any disease or disorder refers, in some embodiments, to ameliorating the disease or disorder (i.e., arresting or reducing the development of the disease or at least one of the clinical symptoms thereof). Treatment may also be considered to include preemptive or prophylactic administration to ameliorate, arrest or prevent the development of the disease or at least one of the clinical symptoms. Treatment can also refer to the lessening of the severity and/or the duration of one or more symptoms of a disease or disorder. In a further feature, the treatment rendered has lower potential for long term side effects over multiple years. In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, adsorption, distribution, metabolism and excretion etc., of the patient to be treated.

"Vehicle" refers to a diluent, excipient or carrier with which a compound is administered to a subject. In some embodiments, the vehicle is pharmaceutically acceptable.

Compounds

Provided herein are compounds of Formula (I) or (II):

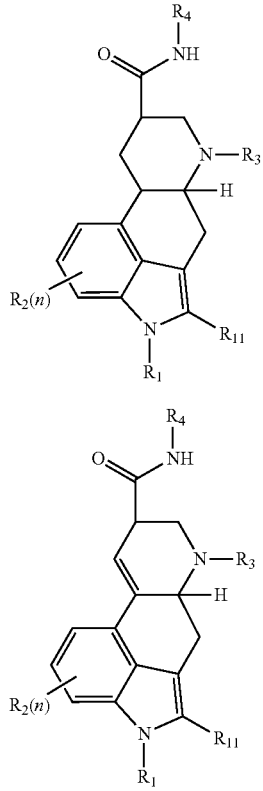

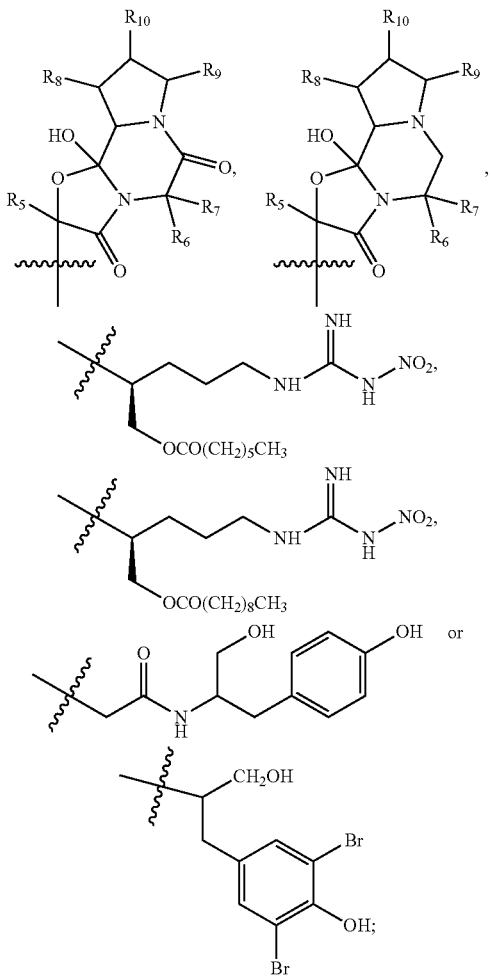

or ion pairs, polymorphs, salts, hydrates or solvates thereof, wherein $R_1$ is hydrogen, $(C_1$-$C_4)$ alkyl, substituted $(C_1$-$C_4)$ alkyl or $(C_1$-$C_4)$ alkyl substituted with one or more fluorine atoms; $R_2$ is alkyl, substituted alkyl, acyl, substituted acyl, halo, heteroalkyl, substituted heteroalkyl, —$NO_2$, —$N_3$, —OH, —$S(O)_kR_{100}$, —$OR_{101}$, —$NR_{102}R_{103}$, —$CONR_{104}R_{105}$, —$CO_2R_{106}$ or —$O_2CR_{107}$; $R_3$ is hydrogen, $(C_1$-$C_3)$ alkyl, $(C_1$-$C_3)$ substituted alkyl or $(C_1$-$C_3)$ alkyl substituted with one or more fluorine atoms; $R_4$ is $R_5$ is $(C_1$-$C_4)$ alkyl or $(C_1$-$C_4)$ substituted alkyl; $R_6$ is hydrogen, $(C_1$-$C_4)$ alkyl, substituted $(C_1$-$C_4)$ alkyl, benzyl or substituted benzyl; $R_7$ is $(C_1$-$C_4)$ alkyl, substituted $(C_1$-$C_4)$ alkyl, benzyl or substituted benzyl; $R_8$ is hydrogen, OH, =O, $(C_1$-$C_4)$ alkyl, $(C_1$-$C_4)$ substituted alkyl, —$CO_2R_{108}$ or —$CONR_{109}R_{110}$; $R_9$ is hydrogen, OH, =O, $(C_1$-$C_4)$ alkyl, $(C_1$-$C_4)$ substituted alkyl, —$CO_2R_{111}$ or —$CONR_{112}R_{113}$; $R_{10}$ is hydrogen, OH, =O, $(C_1$-$C_4)$ alkyl, $(C_1$-$C_4)$ substituted alkyl, —$CO_2R_{114}$ or —$CONR_{115}R_{116}$; $R_{11}$ is $(C_1$-$C_3)$ alkyl substituted with one or more fluorine atoms; $R_{100}$-$R_{116}$ are independently hydrogen, alkyl, substituted alkyl, acyl, substituted acyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; k is 0, 1 or 2; and n is 0, 1, 2 or 3.

In some embodiments, $R_1$ is hydrogen, $(C_1$-$C_4)$ alkyl or $(C_1$-$C_4)$ alkyl substituted with one or more fluorine atoms. In other embodiments, $R_1$ is hydrogen or $(C_1$-$C_4)$ alkyl substituted with one or more fluorine atoms. In still other embodiments, $R_1$ is hydrogen, methyl or methyl substituted with one or more fluorine atoms. In still other embodiments, $R_1$ is hydrogen or methyl substituted with one or more fluorine atoms. In still other embodiments, $R_1$ is hydrogen.

In some embodiments, $R_2$ is alkyl, acyl, halo, $-NO_2$, $-OH$, $-S(O)_kR_{100}$, $-OR_{101}$, $-NR_{102}R_{103}$, $-CONR_{104}R_{105}$, $-CO_2R_{106}$ or $-O_2CR_{107}$. In other embodiments, $R_2$ is alkyl, acyl, halo, $-NO_2$, $-OH$, $-S(O)_kR_{100}$, $-OR_{101}$, $-NR_{102}R_{103}$, $-CONR_{104}R_{105}$, $-CO_2R_{106}$ or $-O_2CR_{107}$ and n is 1. In still other embodiments, $R_2$ is alkyl, halo and $-OR_{101}$ and n is 1. In still other embodiments, n is 0.

In some embodiments, $R_3$ is hydrogen or $(C_1-C_3)$ alkyl. In other embodiments, $R_3$ is hydrogen or methyl. In still other embodiments, $R_3$ is hydrogen or methyl. In still other embodiments, $R_3$ is methyl. In still other embodiments, $R_3$ is hydrogen.

In some embodiments, $R_4$ is

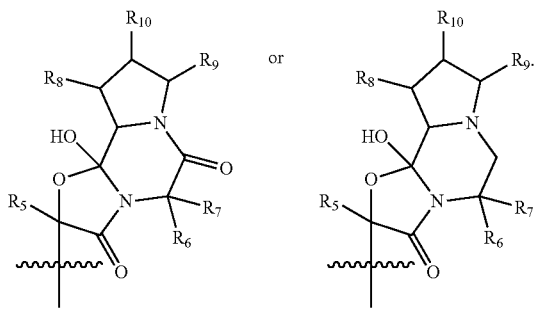

In other embodiments, $R_4$ is

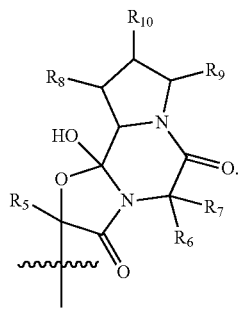

In some embodiments, $R_5$ is $(C_1-C_4)$ alkyl; $R_6$ is hydrogen; $R_7$ is $(C_1-C_4)$ alkyl or substituted $(C_1-C_4)$ alkyl; $R_8$ is hydrogen, OH or $(C_1-C_4)$ alkyl; $R_9$ is hydrogen, OH or $(C_1-C_4)$ alkyl and $R_{10}$ is hydrogen, OH or $(C_1-C_4)$ alkyl. In other embodiments, $R_5$ is $(C_1-C_4)$ alkyl; $R_6$ is hydrogen; $R_7$ is $(C_1-C_4)$ alkyl or substituted $(C_1-C_4)$ alkyl 1; $R_8$ is hydrogen; $R_9$ is hydrogen, and $R_{10}$ is hydrogen. In still other embodiments, $R_5$ is $(C_1-C_4)$ alkyl; $R_6$ is hydrogen; $R_7$ is benzyl or substituted benzyl; $R_8$ is hydrogen, OH or $(C_1-C_4)$ alkyl; $R_9$ is hydrogen, OH or $(C_1-C_4)$ alkyl and $R_{10}$ is hydrogen, OH or $(C_1-C_4)$ alkyl. In still other embodiments, $R_5$ is $(C_1-C_4)$ alkyl; $R_6$ is hydrogen; $R_7$ is benzyl or substituted benzyl; $R_8$ is hydrogen; $R_9$ is hydrogen, and $R_{10}$ is hydrogen.

In some embodiments, $R_{11}$ is methyl substituted with one or more fluorine atoms. In other embodiments, $R_{11}$ is $-CF_3$.

In some embodiments, $R_{100}$-$R_{122}$ are independently hydrogen, alkyl, or substituted alkyl, acyl or substituted acyl. In some embodiments, $R_{100}$-$R_{122}$ are independently hydrogen or alkyl.

In some embodiments, $R_1$ is hydrogen, $(C_1-C_4)$ alkyl or $(C_1-C_4)$ alkyl substituted with one or more fluorine atoms; $R_2$ is alkyl, halo and $-OR_{101}$ and n is 0 or 1; $R_3$ is hydrogen or $(C_1-C_3)$ alkyl; $R_4$ is

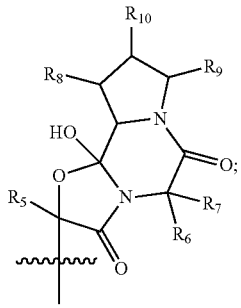

$R_5$ is $(C_1-C_4)$ alkyl; $R_6$ is hydrogen, $(C_1-C_4)$ alkyl or benzyl; $R_7$ is $(C_1-C_4)$ alkyl or benzyl; $R_8$ is hydrogen, OH or $(C_1-C_4)$ alkyl; $R_9$ is hydrogen, OH or $(C_1-C_4)$ alkyl; $R_{10}$ is hydrogen, OH or $(C_1-C_4)$ alkyl; and $R_{11}$ is methyl substituted with one or more fluorine atoms. In other embodiments, $R_1$ is hydrogen, $(C_1-C_4)$ alkyl or $(C_1-C_4)$ alkyl substituted with one or more fluorine atoms; $R_2$ is alkyl, halo and $-OR_{101}$ and n is 0 or 1; $R_3$ is hydrogen or $(C_1-C_3)$ alkyl; $R_4$ is

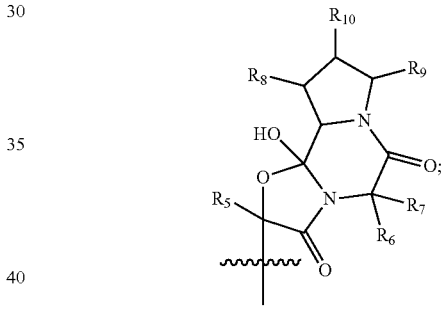

$R_5$ is $(C_1-C_4)$ alkyl; $R_6$ is hydrogen; $R_7$ is $(C_1-C_4)$ alkyl or is $(C_1-C_4)$ substituted alkyl; $R_8$ is hydrogen, OH or $(C_1-C_4)$ alkyl; $R_9$ is hydrogen, OH or $(C_1-C_4)$ alkyl; $R_{10}$ is hydrogen, OH or $(C_1-C_4)$ alkyl; and $R_{11}$ is methyl substituted with one or more fluorine atoms. In still other embodiments, $R_1$ is hydrogen, $(C_1-C_4)$ alkyl or $(C_1-C_4)$ alkyl substituted with one or more fluorine atoms; $R_2$ is alkyl, halo and $-OR_{101}$ and n is 0 or 1; $R_3$ is hydrogen or $(C_1-C_3)$ alkyl; $R_4$ is

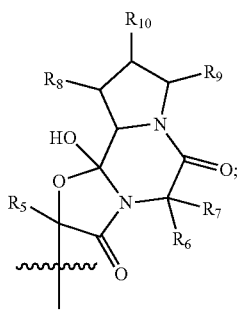

$R_5$ is $(C_1-C_4)$ alkyl; $R_6$ is hydrogen; $R_7$ is $(C_1-C_4)$ alkyl or is $(C_1-C_4)$ substituted alkyl; $R_8$ is hydrogen; $R_9$ is hydrogen; $R_{10}$ is hydrogen; and $R_{11}$ is methyl substituted with one or more fluorine atoms. In still other embodiments, $R_1$ is hydrogen, $(C_1-C_4)$ alkyl or $(C_1-C_4)$ alkyl substituted with one or more fluorine atoms; $R_2$ is alkyl, halo and $-OR_{101}$ and n is 0 or 1; $R_3$ is hydrogen or $(C_1-C_3)$ alkyl; $R_4$ is

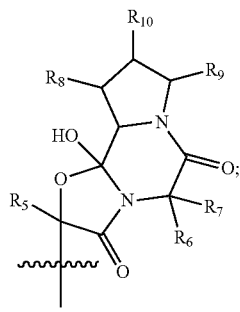

$R_5$ is $(C_1-C_4)$ alkyl; $R_6$ is hydrogen; $R_7$ is benzyl or substituted benzyl; $R_8$ is hydrogen, OH or $(C_1-C_4)$ alkyl; $R_9$ is hydrogen, OH or $(C_1-C_4)$ alkyl; $R_{10}$ is hydrogen, OH or $(C_1-C_4)$ alkyl; and $R_{11}$ is methyl substituted with one or more fluorine atoms. In still other embodiments, $R_1$ is hydrogen, $(C_1-C_4)$ alkyl or $(C_1-C_4)$ alkyl substituted with one or more fluorine atoms; $R_2$ is alkyl, halo and $-OR_{101}$ and n is 0 or 1; $R_3$ is hydrogen or $(C_1-C_3)$ alkyl; $R_4$ is

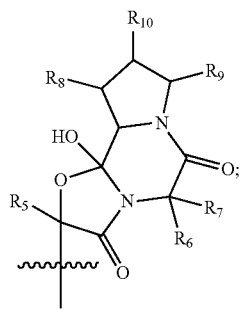

$R_5$ is $(C_1-C_4)$ alkyl; $R_6$ is hydrogen; $R_7$ is benzyl or substituted benzyl; $R_8$ is hydrogen; $R_9$ is hydrogen; $R_{10}$ is hydrogen; and $R_{11}$ is methyl substituted with one or more fluorine atoms.

In some embodiments, $R_1$ is hydrogen, $(C_1-C_4)$ alkyl or $(C_1-C_4)$ alkyl substituted with one or more fluorine atoms; $R_2$ is alkyl, acyl, halo, $-NO_2$, $-OH$, $-S(O)_kR_{100}$, $-OR_{101}$, $-NR_{102}R_{103}$, $-CONR_{104}R_{105}$, $-CO_2R_{106}$ or $-O_2CR_{107}$; $R_3$ is hydrogen or $(C_1-C_3)$ alkyl; $R_4$ is

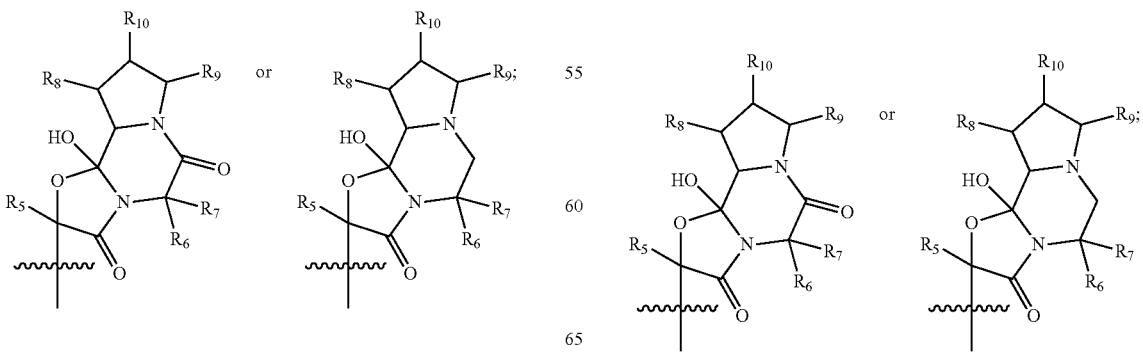

$R_5$ is $(C_1-C_4)$ alkyl; $R_6$ is hydrogen, $(C_1-C_4)$ alkyl or benzyl; $R_7$ is $(C_1-C_4)$ alkyl or benzyl; $R_8$ is hydrogen, OH or $(C_1-C_4)$ alkyl; $R_9$ is hydrogen, OH or $(C_1-C_4)$ alkyl; $R_{10}$ is hydrogen, OH or $(C_1-C_4)$ alkyl; and $R_{11}$ is methyl substituted with one or more fluorine atoms.

In other embodiments, $R_1$ is hydrogen, $(C_1-C_4)$ alkyl or $(C_1-C_4)$ alkyl substituted with one or more fluorine atoms; $R_3$ is hydrogen or $(C_1-C_3)$ alkyl; $R_4$ is

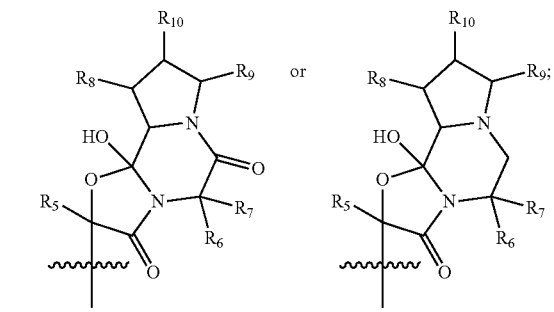

$R_5$ is $(C_1-C_4)$ alkyl; $R_6$ is hydrogen, $(C_1-C_4)$ alkyl or benzyl; $R_7$ is $(C_1-C_4)$ alkyl or benzyl; $R_8$ is hydrogen, OH or $(C_1-C_4)$ alkyl; $R_9$ is hydrogen, OH or $(C_1-C_4)$ alkyl; $R_{10}$ is hydrogen, OH or $(C_1-C_4)$ alkyl; $R_{11}$ is methyl substituted with one or more fluorine atoms; and n is 0. In still other embodiments, $R_1$ is hydrogen, $(C_1-C_4)$ alkyl or $(C_1-C_4)$ alkyl substituted with one or more fluorine atoms; $R_3$ is hydrogen or $(C_1-C_3)$ alkyl; $R_4$ is

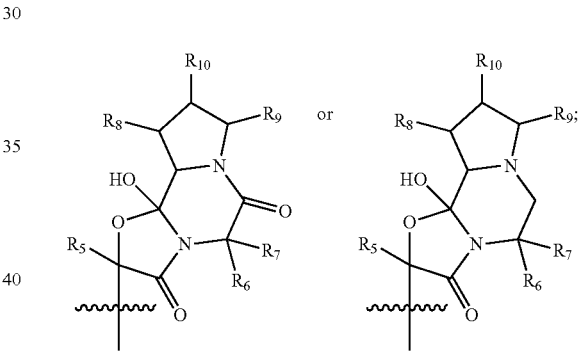

$R_5$ is $(C_1-C_4)$ alkyl; $R_6$ is hydrogen; $R_7$ is $(C_1-C_4)$ alkyl, substituted $(C_1-C_4)$ alkyl, benzyl or substituted benzyl; $R_8$ is hydrogen, OH or $(C_1-C_4)$ alkyl; $R_9$ is hydrogen, OH or $(C_1-C_4)$ alkyl; $R_{10}$ is hydrogen, OH or $(C_1-C_4)$ alkyl; $R_{11}$ is methyl substituted with one or more fluorine atoms; and n is 0. In still other embodiments, $R_1$ is hydrogen, $(C_1-C_4)$ alkyl or $(C_1-C_4)$ alkyl substituted with one or more fluorine atoms; $R_3$ is hydrogen or $(C_1-C_3)$ alkyl; $R_4$ is $R_5$ is $(C_1\text{-}C_4)$ alkyl; $R_6$ is hydrogen; $R_7$ is $(C_1\text{-}C_4)$ alkyl, substituted $(C_1\text{-}C_4)$ alkyl, benzyl or substituted benzyl; $R_8$ is hydrogen; $R_9$ is hydrogen; $R_{10}$ is hydrogen; $R_{11}$ is methyl substituted with one or more fluorine atoms; and n is 0.

In still other embodiments, $R_1$ is hydrogen; $R_2$ is alkyl, acyl, halo, $-NO_2$, $-OH$, $-S(O)_k R_{100}$, $-NR_{102}R_{103}$, $-CONR_{104}R_{105}$, $-CO_2R_{106}$ or $-O_2CR_{107}$; $R_3$ is hydrogen or $(C_1\text{-}C_3)$ alkyl; $R_4$ is

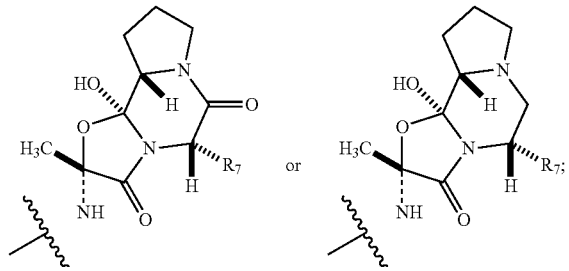

$R_7$ is $(C_1\text{-}C_4)$ alkyl or benzyl; $R_8$ is hydrogen, OH or $(C_1\text{-}C_4)$ alkyl; $R_9$ is hydrogen, OH or $(C_1\text{-}C_4)$ alkyl; $R_{10}$ is hydrogen, OH or $(C_1\text{-}C_4)$ alkyl; and $R_{11}$ is methyl substituted with one or more fluorine atoms.

In still other embodiments, $R_1$ is hydrogen, $(C_1\text{-}C_4)$ alkyl or $(C_1\text{-}C_4)$ alkyl substituted with one or more fluorine atoms; $R_2$ is alkyl, acyl, halo, $-NO_2$, $-OH$, $-S(O)_k R_{100}$, $-OR_{101}$, $-NR_{102}R_{103}$, $-CONR_{104}R_{105}$, $-CO_2R_{106}$ or $-O_2CR_{107}$; $R_3$ is methyl; $R_4$ is

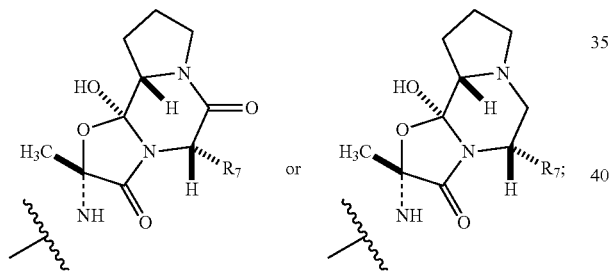

$R_7$ is $(C_1\text{-}C_4)$ alkyl or benzyl; and $R_{11}$ is methyl substituted with one or more fluorine atoms.

In still other embodiments, $R_1$ is hydrogen $(C_1\text{-}C_4)$ alkyl or $(C_1\text{-}C_4)$ alkyl substituted with one or more fluorine atoms; $R_2$ is alkyl, acyl, halo, $-NO_2$, $-OH$, $-S(O)_k R_{100}$, $-OR_{101}$, $-NR_{102}R_{103}$, $-CONR_{104}R_{105}$, $-CO_2R_{106}$ or $-O_2CR_{107}$; $R_3$ is hydrogen or $(C_1\text{-}C_3)$ alkyl; $R_4$ is

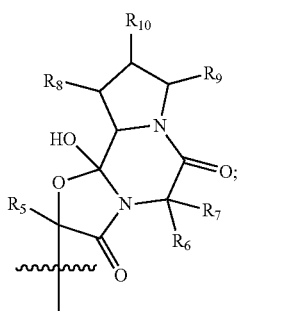

$R_5$ is $(C_1\text{-}C_4)$ alkyl; $R_6$ is hydrogen, $(C_1\text{-}C_4)$ alkyl or benzyl; $R_7$ is $(C_1\text{-}C_4)$ alkyl or benzyl; $R_8$ is hydrogen, OH, or $(C_1\text{-}C_4)$ alkyl; $R_9$ is hydrogen, OH, $(C_1\text{-}C_4)$ alkyl; $R_{10}$ is hydrogen, OH or $(C_1\text{-}C_4)$ alkyl; and $R_{11}$ is methyl substituted with one or more fluorine atoms. In still other embodiments, $R_1$ is hydrogen $(C_1\text{-}C_4)$ alkyl or $(C_1\text{-}C_4)$ alkyl substituted with one or more fluorine atoms; $R_2$ is alkyl, acyl, halo, $-NO_2$, $-OH$, $-S(O)_k R_{100}$, $-OR_{101}$, $-NR_{102}R_{103}$, $-CONR_{104}R_{105}$, $-CO_2R_{106}$ or $-O_2CR_{107}$; $R_3$ is hydrogen or $(C_1\text{-}C_3)$ alkyl; $R_4$ is

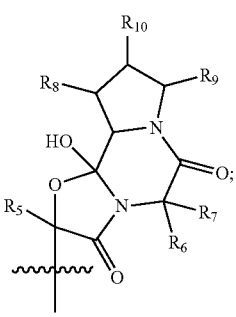

$R_5$ is $(C_1\text{-}C_4)$ alkyl; $R_6$ is hydrogen, $R_7$ is $(C_1\text{-}C_4)$ alkyl or $(C_1\text{-}C_4)$ substituted alkyl; $R_8$ is hydrogen; $R_9$ is hydrogen; $R_{10}$ is hydrogen; and $R_{11}$ is methyl substituted with one or more fluorine atoms. In still other embodiments, $R_1$ is hydrogen $(C_1\text{-}C_4)$ alkyl or $(C_1\text{-}C_4)$ alkyl substituted with one or more fluorine atoms; $R_2$ is alkyl, acyl, halo, $-NO_2$, $-OH$, $-S(O)_k R_{100}$, $-OR_{101}$, $-NR_{102}R_{103}$, $-CONR_{104}R_{105}$, $-CO_2R_{106}$ or $-O_2CR_{107}$; $R_3$ is hydrogen or $(C_1\text{-}C_3)$ alkyl; $R_4$ is

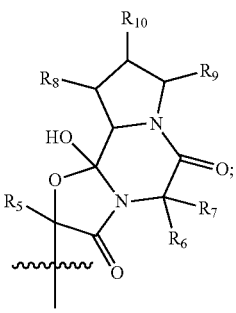

$R_5$ is $(C_1\text{-}C_4)$ alkyl; $R_6$ is hydrogen, $R_7$ is benzyl or $(C_1\text{-}C_4)$ substituted benzyl; $R_8$ is hydrogen; $R_9$ is hydrogen; $R_{10}$ is hydrogen; and $R_{11}$ is methyl substituted with one or more fluorine atoms.

In other embodiments, $R_1$ is hydrogen, methyl or methyl substituted with one or more fluorine atoms; $R_3$ is hydrogen or $(C_1\text{-}C_3)$ alkyl; $R_4$ is

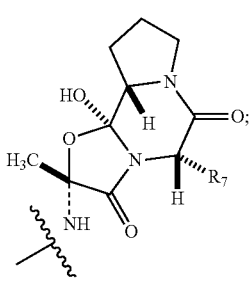

$R_7$ is $(C_1\text{-}C_4)$ alkyl or benzyl; $R_{11}$ is methyl substituted with one or more fluorine atoms; and n is 0.

In still other embodiments, $R_1$ is hydrogen or $(C_1\text{-}C_4)$ alkyl substituted with one or more fluorine atoms; $R_3$ is hydrogen or $(C_1\text{-}C_3)$ alkyl; $R_4$ is

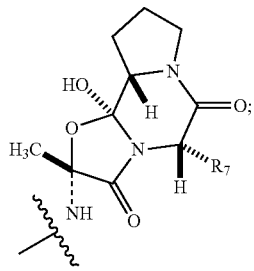

$R_5$ is $(C_1\text{-}C_4)$ alkyl; $R_7$ is $(C_1\text{-}C_4)$ alkyl or benzyl; $R_{11}$ is methyl substituted with one or more fluorine atoms; and n is 0.

In still other embodiments, $R_1$ is hydrogen; $R_3$ is hydrogen or methyl; $R_4$ is

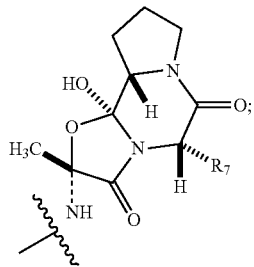

$R_7$ is $(C_1\text{-}C_4)$ alkyl or benzyl; $R_{11}$ is methyl substituted with one or more fluorine atoms; and n is 0.

In some of the above embodiments, $R_{11}$ is —$CF_3$.

In some embodiments, the 2-trifluoro methyl (i.e., the hydrogen atom adjacent to the indole nitrogen of the parent compound is substituted with trifluoromethyl) analog of methysergide, dihydromethysergide, ergocristine, dihydroergocristine, α-ergocristine, α-dihydroergocristine, β-ergocristine, β-dihydroergocristine, dihydroergocorine and dihydroergocorine are provided.

In some embodiments, a compound having the structure:

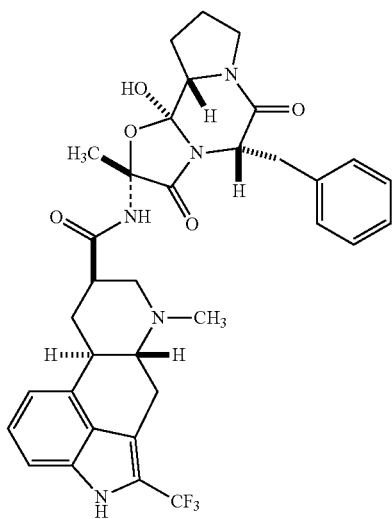

is provided.

In other embodiments, a compound having the structure:

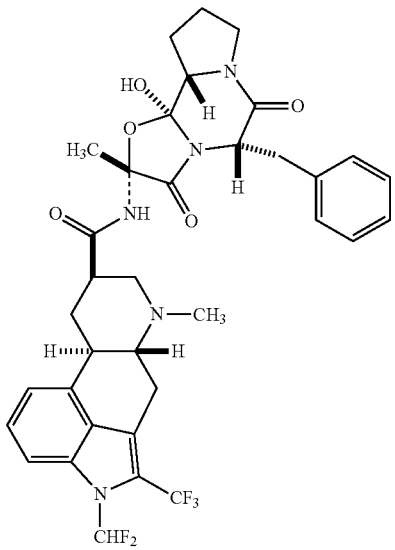

is provided.

In still other embodiments, a compound having the structure:

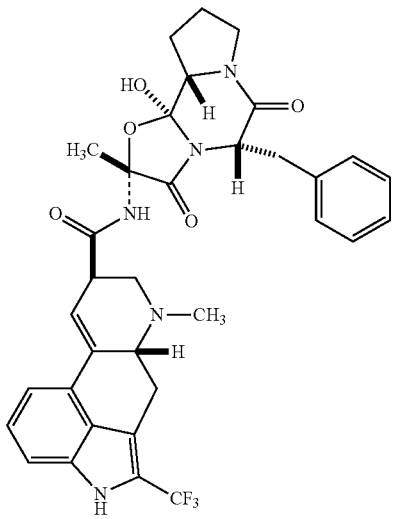

is provided.

In still other embodiments, a compound having the structure:
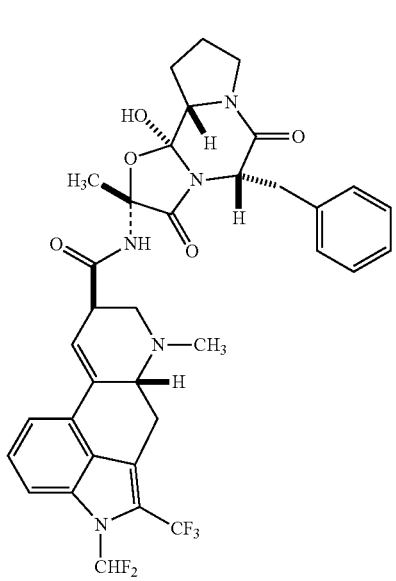
is provided.
In some embodiments, a compound having the structure:
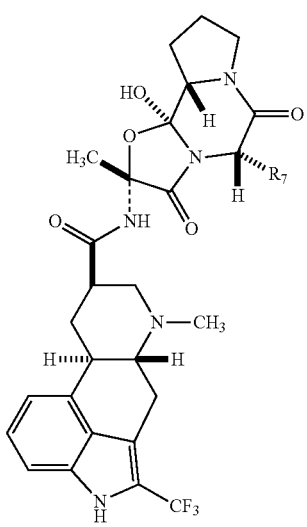
where $R_7$ is $(C_1$-$C_4)$ alkyl is provided.
In other embodiments, a compound having the structure:
where $R_7$ is $(C_1$-$C_4)$ alkyl is provided.
In still other embodiments, a compound having the structure:
where $R_7$ is $(C_1$-$C_4)$ alkyl is provided.

In still other embodiments, a compound having the structure:

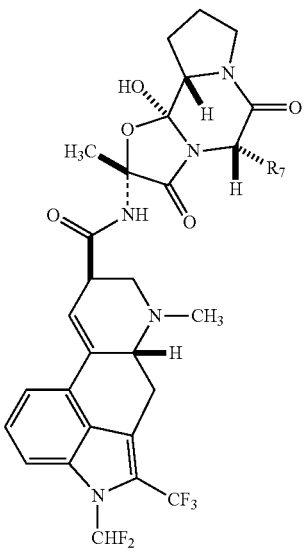

where $R_7$ is $(C_1-C_4)$ alkyl is provided.

Exemplary methods for the preparation of compounds of Formula (I) and (II) for use in the compositions and methods provided herein are described below and in the Examples but other methods known in the art can be used to prepare the fluoroergoline derivatives disclosed herein.

In some embodiments, direct functionalization of 2-unsubstituted analogs of compounds of Formula (I) and (II) (e.g., compounds of Formula (III) and (IV)), for example, with an alkyl halide under basic conditions can be used to provide the compounds of Formula (I) and (II).

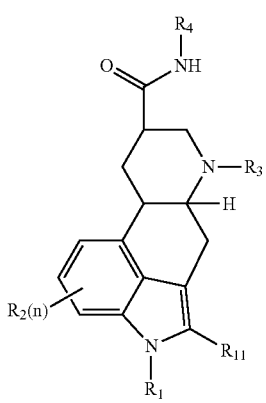
(I)

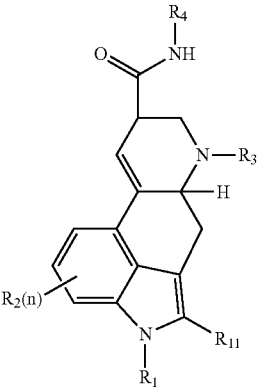
(II)

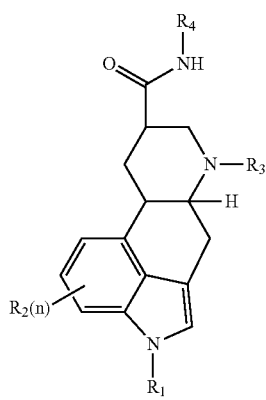
(III)

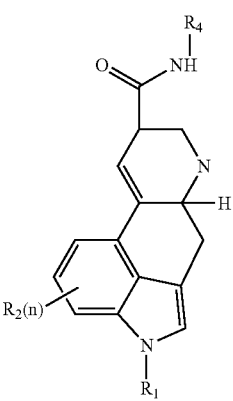
(IV)

In other embodiments, carboxylic acids (V) and (VI) which can be prepared by methods well known to those of skill in the art can be used provide compounds of Formulas (I) and (II) by acylation reactions.

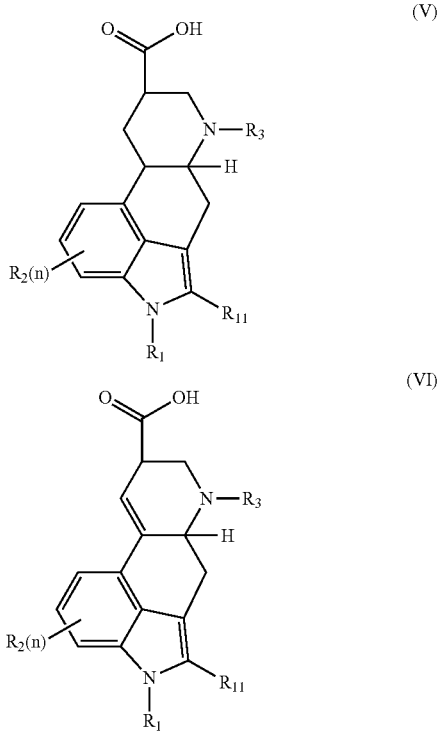

Many methods exist for conversion of carboxylic (IV) and (V) to compounds of Formulas (I) and (II), respectively. Accordingly, preparation of amides (I) and (II) from carboxylic acids (I) and (II) are well within the ambit of the skilled artisan.

Compositions and Methods of Administration

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration.

In addition, the compounds may be formulated as the sole active ingredient in the composition or may be combined with other active ingredients.

The compositions contain one or more compounds provided herein. The compounds are, in some embodiments, formulated into suitable preparations such as solutions, suspensions, tablets, dispersible tablets, pills, capsules, powders, sustained release formulations or elixirs, for oral administration or in sterile solutions or suspensions for parenteral administration, as well as topical administration, transdermal administration and oral inhalation via nebulizers, pressurized metered dose inhalers and dry powder inhalers. In some embodiments, the compounds described above are formulated into compositions using techniques and procedures well known in the art (see, e.g., Ansel Introduction to Pharmaceutical Dosage Forms, Seventh Edition (1999).

In the compositions, effective concentrations of one or more compounds or derivatives thereof is (are) mixed with a suitable vehicle. The compounds may be derivatized as the corresponding salts, esters, enol ethers or esters, acetals, ketals, orthoesters, hemiacetals, hemiketals, acids, bases, solvates, ion-pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated therefrom for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In some embodiments, a therapeutically effective dosage should produce a serum concentration of active ingredient of from about 0.001 ng/ml to about 50-200 μg/ml. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethylsulfoxide (DMSO), using surfactants or surface modifiers, such as TWEEN®, complexing agents such as cyclodextrin or dissolution by enhanced ionization (i.e. dissolving in aqueous sodium bicarbonate). Derivatives of the compounds, such as prodrugs of the compounds may also be used in formulating effective compositions.

Upon mixing or addition of the compound(s), the resulting mixture may be a solution, suspension, emulsion or the like. The form of the resulting mixture depends upon a number of factors, including the intended mode of administration and the solubility of the compound in the selected vehicle. The effective concentration is sufficient for ameliorating the symptoms of the disease, disorder or condition treated and may be empirically determined.

The compositions are provided for administration to humans and animals in indication appropriate dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or derivatives thereof. The therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 0.1-95%, in another embodiment 0.4-10%.

In certain embodiments, the compositions are lactose-free compositions containing excipients that are well known in the art and are listed, for example, in the U.S. Pharmacopeia (USP) 25-NF20 (2002). In general, lactose-free compositions contain active ingredients, a binder/filler, and a lubricant in compatible amounts. Particular lactose-free dosage forms contain active ingredients, microcrystalline cellulose, pregelatinized starch, and magnesium stearate.

Further provided are anhydrous compositions and dosage forms comprising active ingredients, since water can facilitate the degradation of some compounds. For example, the addition of water (e.g., 5%) is widely accepted as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions.

An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene laural ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The compound, or derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, $H_2$ blockers, and diuretics. The active ingredient is a compound or derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are nonaqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of nonaqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or polyalkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a acetal. Alcohols used in these formulations are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the compositions to be administered may also contain minor amounts of nontoxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (Tween® 80). A sequestering or chelating agent of metal ions includes EDTA. Carriers also include ethyl alcohol, polyethylene glycol and propylene glycol for water miscible vehicles; and sodium hydroxide, hydrochloric acid, citric acid or lactic acid for pH adjustment.

The concentration of compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In some embodiments, a therapeutically effective dosage is formulated to contain a concentration of at least about 0.01% w/w up to about 90% w/w or more, in certain embodiments more than 0.1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In some embodiments, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321: 574 (1989)). In other embodiments, polymeric materials can be used. In other embodiments, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984)). In some embodiments, a controlled release device is introduced into a subject in proximity of the site of inappropriate immune activation or a tumor. Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbital, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

Oral inhalation formulations of the compounds or derivatives suitable for inhalation include metered dose inhalers, dry powder inhalers and liquid preparations for administration from a nebulizer or metered dose liquid dispensing system. For both metered dose inhalers and dry powder inhalers, a crystalline form of the compounds or derivatives is the preferred physical form of the drug to confer longer product stability.

In addition to particle size reduction methods known to those skilled in the art, crystalline particles of the compounds or derivatives can be generated using supercritical fluid processing which offers significant advantages in the production of such particles for inhalation delivery by producing respirable particles of the desired size in a single step. (e.g., International Publication No. WO2005/025506). A controlled particle size for the microcrystals can be selected to ensure that a significant fraction of the compounds or derivatives is deposited in the lung. In some embodiments, these particles have a mass median aerodynamic diameter of about 0.1 to about 10 microns, in other embodiments, about 1 to about 5 microns and still other embodiments, about 1.2 to about 3. microns.

Inert and non-flammable HFA propellants are selected from HFA 134a (1,1,1,2-tetrafluoroethane) and HFA 227e (1,1,1,2,3,3,3-heptafluoropropane) and provided either alone or as a ratio to match the density of crystal particles of the compounds or derivatives. A ratio is also selected to ensure that the product suspension avoids detrimental sedimentation or cream (which can precipitate irreversible agglomeration) and instead promote a loosely flocculated system, which is easily dispersed when shaken. Loosely fluctuated systems are well regarded to provide optimal stability for pMDI canisters. As a result of the formulation's properties, the formulation contained no ethanol and no surfactants/stabilizing agents.

The formulation of the compounds or derivatives can be administered to patients using TEMPO™, a novel breath activated metered dose inhaler. TEMPO™ overcomes the variability associated with standard pressurized metered dose inhalers (pMDI), and achieves consistent delivery of drug to the lung periphery where it can be systemically absorbed. To do so, TEMPO™ incorporates four novel features: 1) breath synchronous trigger—can be adjusted for different drugs and target populations to deliver the drug at a specific part of the inspiratory cycle, 2) plume control—an impinging jet to slow down the aerosol plume within the actuator, 3) vortexing chamber—consisting of porous wall, which provides an air cushion to keep the slowed aerosol plume suspended and air inlets on the back wall which drive the slowed aerosol plume into a vortex pattern, maintaining the aerosol in suspension and allowing the particle size to reduce as the HFA propellant evaporates, and 4) dose counter—will determine the doses remaining and prevent more than the intended maximum dose to be administered from any one canister.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other excipients can also be administered.

For nasal administration, the preparation may contain an esterified phosphonate compound dissolved or suspended in a liquid carrier, in particular, an aqueous carrier, for aerosol application. The carrier may contain solubilizing or suspending agents such as propylene glycol, surfactants, absorption enhancers such as lecithin or cyclodextrin, or preservatives.

Solutions, particularly those intended for ophthalmic use, may be formulated as 0.01%-10% isotonic solutions, pH about 5-7.4, with appropriate salts.

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433 and 5,860,957.

For example, dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same substance and by the same methods as for formulations for oral administration.

The compounds provided herein, or derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316, 652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

Dosages

In human therapeutics, the physician will determine the dosage regimen that is most appropriate according to a preventive or curative treatment and according to the age, weight, stage of the disease and other factors specific to the subject to be treated. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form. The amount of active ingredient in the formulations provided herein, which will be effective in the prevention or treatment of a disorder or one or more symptoms thereof, will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject.

Exemplary doses of a formulation include milligram or microgram amounts of the active compound per kilogram of subject (e.g., from about 1 micrograms per kilogram to about 50 milligrams per kilogram, from about 10 micrograms per kilogram to about 30 milligrams per kilogram, from about 100 micrograms per kilogram to about 10 milligrams per kilogram, or from about 100 microgram per kilogram to about 5 milligrams per kilogram).

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

Methods of Use of the Compounds and Compositions

Methods of treating, preventing, or ameliorating one or more symptoms of diseases including, for example, migraine, ALS, Parkinson's disease, extra-pyramidal disorders, depression, nausea, restless legs syndrome, insomnia, aggression, Huntington's disease, dystonia, parsomnia and hyperlactinemia are also provided herein. In practicing the methods, therapeutically effective amounts of the compounds or compositions, described herein, supra, are administered.

Also provided are methods for antagonizing receptors including 5-$HT_{2B}$ receptors and adrenergic alpha$_{1A}$, alpha$_{1D}$, alpha$_{2C}$, alpha$_{2A}$ and alpha$_{2B}$ receptors using the compounds and compositions, described herein. In practicing the methods, therapeutically effective amounts of the compounds or compositions, described herein, supra, are administered.

Also provided are methods for agonizing the 5-$HT_{1D}$ and 5-$HT_{1B}$ receptors using the compounds and compositions described herein. In some embodiments, methods of selectively agonizing the 5-$HT_{1D}$ receptor over the 5-$HT_{1B}$ receptor using the compounds and compositions described herein are provided. In other embodiments, the compounds and compositions described herein selectively agonizes the 5-$HT_{1D}$ receptor over the 5-$HT_{1B}$ receptor in a ratio of about 4:1. In still other embodiments, the compounds and compositions described herein selectively agonizes the 5-$HT_{1D}$ receptor over the 5-$HT_{1B}$ receptor in a ratio of about 30:1.

In still other embodiments, methods of reducing agonism of dopamine receptors when compared to agonism of dopamine receptors by other ergolines, such as, for example, dihydroergotamine using the compounds and compositions described herein is provided herein. In some embodiments, the dopamine receptor is the $D_2$ receptor. In practicing the methods, therapeutically effective amounts of the compounds or compositions are administered.

Combination Therapy

The compounds and compositions disclosed herein may also be used in combination with one or more other active ingredients. In certain embodiments, the compounds may be administered in combination, or sequentially, with another therapeutic agent. Such other therapeutic agents include those known for treatment, prevention, or amelioration of one or more symptoms associated with migraine.

It should be understood that any suitable combination of the compounds and compositions provided herein with one or more of the above therapeutic agents and optionally one or more further pharmacologically active substances are considered to be within the scope of the present disclosure. In some embodiments, the compounds and compositions provided herein are administered prior to or subsequent to the one or more additional active ingredients.

It should also be understood that any suitable combination of the compounds and compositions provided herein may be used with other agents to agonize and or antagonize the receptors mentioned above.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety.

The following examples are provided for illustrative purposes only and are not intended to limit the scope of the invention.

EXAMPLES

Example 1

Preparation of 2-$CF_3$-Dihydroergotamine

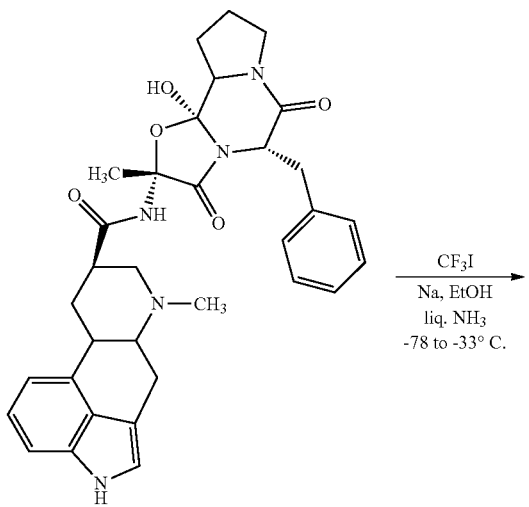

-continued

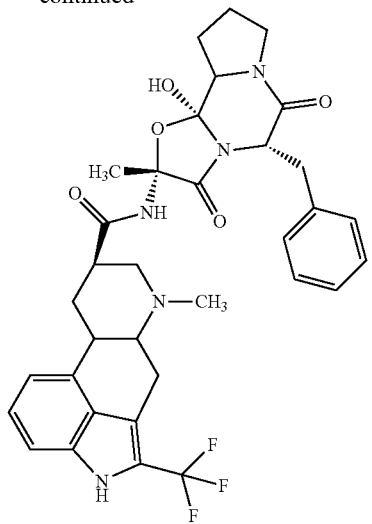

To a solution of sodium metal (164.5 mg, 6.85 mmol) in liquid ammonia (50 mL) under $N_2$ at −78° C. was added absolute ethanol (1.40 mL, 24 mmol) dropwise within 15 min and then the reaction mixture was warmed to −33° C. Stirring at this temperature for 40 min decolorized the initially dark blue solution. The solution was cooled to −78° C. and dihydroergotamine (400 mg, 0.69 mmol) was subsequently added into the flask in portions. The reaction mixture was stirred at −78° C. until it became a clear solution, and then trifluormethyl iodide (1.34 g, 6.85 mmol) was introduced as condensed from a cylinder within 5 min. The temperature of the reaction was allowed to reach −33° C. and was kept at this temperature for 14 h while stirring. The solution was cooled to −78° C. again and ammonium carbonate (1.54 g, 16 mmol) was added. After stirring for 1 h at −78° C., the system was placed under vacuum, the suspension was carefully heated (the temperature was maintained below −30° C.) and the ammonia was slowly evaporated. The remaining solid residue was triturated with methylene chloride (80 mL) containing 1% methanol. The organic phase was filtered off, and evaporated in vacuo. The residue was purified twice by column chromatography (silica gel, 6 g, 95:5 methylene chloride/MeOH) to afford 2-$CF_3$-dihydroergotamine (40 mg, 77% purity as assessed by $^1$H NMR analysis) as an amorphous yellow solid. This product was combined with two more batches and purified together by HPLC to give 2-$CF_3$-dihydroergotamine (14 mg, 1%). HPLC 97.1% (AUC); ESI MS m/z 652 $[C_{34}H_{36}F_3N_5O_5+H]^+$; $^1$H NMR (400 MHz, $CDCl_3$) δ ppm 8.18 (s, 1H), 7.42 (d, J=7.0 Hz, 2H), 7.33 (t, J=7.8 Hz, 1H), 7.20-7.28 (m, 3H), 7.14-7.20 (m, 1H), 7.01 (d, J=7.0 Hz, 1H), 6.49 (d, J=1.8 Hz, 1H), 6.25 (s, 1H), 4.72 (t, J=6.0 Hz, 1H), 3.60-3.71 (m, 1H), 3.45-3.59 (m, 4H), 3.24 (dd, J=14.1, 6.3 Hz, 1H), 3.09-3.16 (m, 1H), 2.87-2.97 (m, 1H), 2.64-2.81 (m, 3H), 2.50 (s, 3H), 2.43 (t, J=11.4 Hz, 1H), 2.22-2.31 (m, 1H), 1.98-2.20 (m, 3H), 1.75-1.88 (m, 1H), 1.64-1.74 (m, 1H), 1.58 (s, 3H).

Example 2

Agonist Activity at the 5-$HT_{2B}$ Receptor with 2-$CF_3$-Dihydroergotamine

An Aequorin assay was conducted to monitor agonist activity for 2-$CF_3$-dihydroergotamine against the human 5-$HT_{2B}$ receptor. The agonist assay was completed with 2-$CF_3$-dihydroergotamine at concentrations between 0.01 nM and 20,000 nM. Percentage activation values were determined for 2-$CF_3$ dihydroergotamine at the 5-$HT_{2B}$ receptor. Agonist selectivity was determined upon mixing CHO-K1 cells coexpressing mitochondrial apoaequorin and recombinant human 5-$HT_{2B}$ receptor with 2-$CF_3$-dihydroergotamine. The resulting emission of light was recorded using a luminometer. Agonist percentage activation determinations were obtained by comparing with the $E_{max}$ of the reference agonist α-methyl-5-HT. The assay was performed by EuroScreen S.A., Belgium.

The data is summarized in FIG. 1 which illustrates potent agonism of the 5-$HT_{2B}$ receptor for the α-methyl-5-HT (known potent agonist of $EC_{50}$ of 1.01 nM). Unexpectedly, 2-$CF_3$-dihydroergotamine shows no agonist activity.

Example 3

Competitive Antagonist Activity of the 5-$HT_{2B}$ Receptor with 2-$CF_3$-Dihydroergotamine An Aequorin assay was conducted to monitor antagonist activity for 2-$CF_3$-dihydroergotamine against the human 5-$HT_{2B}$ receptor. The antagonist assay was completed with 2-$CF_3$-dihydroergotamine at final concentrations between 0.005 nM and 10,000 nM. Percentage inhibition values were determined for 2-$CF_3$ dihydroergotamine on the 5-$HT_{2B}$ receptor. CHO-K1 cells coexpressing mitochondrial apoaequorin and recombinant human 5-$HT_{2B}$ receptor was mixed with 2-$CF_3$-dihydroergotamine. A reference agonist at its $EC_{80}$ was then injected into the mixture of cells and 2-$CF_3$-dihydroergotamine. The resulting emission of light was recorded using a luminometer. The assay was performed by EuroScreen S.A., Belgium.

Figure 2:
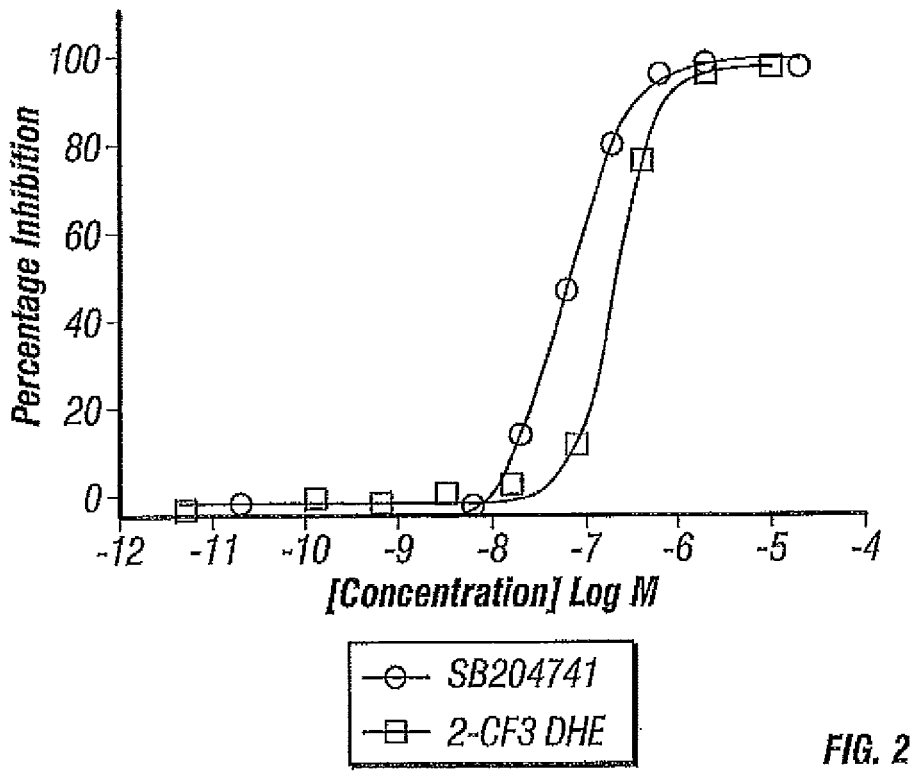
FIG. 2 illustrates potent antagonism of the 5-$HT_{2B}$ receptor by 2-$CF_3$-dihydroergotamine.

The data is summarized in FIG. 2 which illustrates potent antagonism of the 5-$HT_{2B}$ receptor for the SB204741 (known 5-$HT_{2B}$ antagonist of $IC_{50}$ of 28.83 nM), confirming assay validity. Furthermore, 2-$CF_3$-dihydroergotamine behaves as an antagonist with $IC_{50}$ of 204.5 nM.

Example 4

Agonist Activity at the 5-$HT_{1B}$ and 5-$HT_{1D}$ Receptors with 2-$CF_3$-Dihydroergotamine GTPγS assays were conducted to monitor agonist activities for 2-$CF_3$-dihydroergotamine against the human 5-$HT_{1B}$ and 5-$HT_{1D}$ receptors, at final concentrations between 0.005 nM and 10,000 nM. 2-$CF_3$-dihydroergotamine was mixed with a mixture of recombinant 5-$HT_{1B}$ and 5-$HT_{1D}$ membrane extracts and GDP, and a mixture of GTPγS and PVT-WGA beads. The mixture was shaken for 2 minutes prior to a 60 min incubation. It was then centrifuged for 10 minutes and counted for 1 minute with a Perkin Elmer TopCount reader. The resulting emission of light was recorded using a luminometer. Agonist percentage activation determinations were obtained by comparing with the $E_{max}$ of the reference agonist α-methyl-5-HT. The assay was performed by EuroScreen S.A., Belgium.

Figure 3:
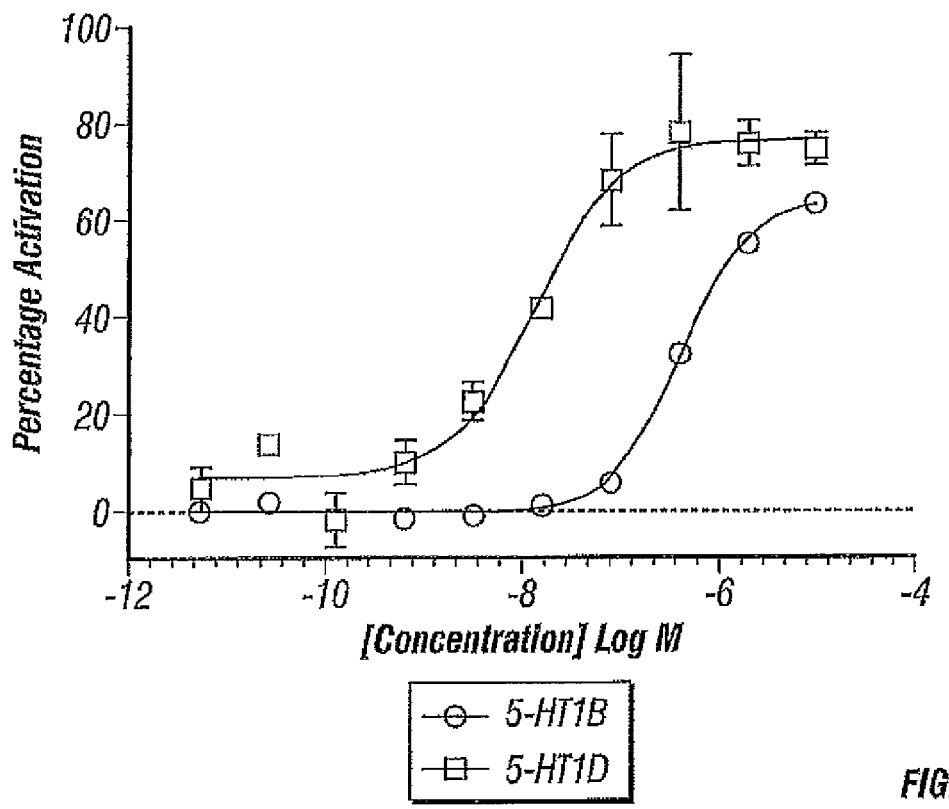
FIG. 3 illustrates that 2-CF3-dihydroergotamine behaves as an agonist with both 5-$HT_{1B}$ and 5-$HT_{1D}$ and affords greater selectivity for 5-$HT_{1D}$ over 5-$HT_{1B}$ (5-$HT_{1D}$:5-$HT_{1B}$ (30:1)).

The data are summarized in FIG. 3. 2-CF3-dihydroergotamine behaved as an agonist with both 5-$HT_{1B}$ ($EC_{50}$ of 406 nM) and 5-$HT_{1D}$ ($EC_{50}$ of 13.6 nM). Unexpectedly, 2-$CF_3$-dihydroergotamine displayed high selectivity of 5-$HT_{1D}$:5-$HT_{1B}$ (30:1).

Example 5

Agonist Activity at the $D_2$ Receptor with 2-$CF_3$-Dihydroergotamine

The assay was performed analogously to the assay described in Example 4. Both dihydroergotamine ($EC_{50}$ of 8.35 nM) and 2-CF3-dihydroergotamine ($EC_{50}$ of 218 nM) have agonist activity at the D2 receptor. Unexpectedly, substitution with 2-CF3 caused significant increase in $EC_{50}$.

Example 6

Competitive Antagonist Activity of the Adrenergic Receptors $\alpha_{1A}$ and $\alpha_{1D}$ Receptors with 2-$CF_3$-Dihydroergotamine The assays were performed analogously to the assay described in Example 3. 2-CF3-dihydroergotamine is a significant antagonist of $\alpha_{1A}$ ($IC_{50}$ of 207 nM) and $\alpha_{1D}$ ($IC_{50}$ of 40.19 nM) receptors.

Example 7

Competitive Antagonist Activity of the Adrenergic Receptors $\alpha_{2A}$, $\alpha_{2B}$ and $\alpha_{2C}$ Receptors with 2-$CF_3$-Dihydroergotamine GTPγS assays were conducted to monitor antagonist activity for 2-$CF_3$-dihydroergotamine against the human $\alpha_{2A}$, $\alpha_{2B}$ and $\alpha_{2C}$ receptors. 2-$CF_3$-dihydroergotamine behaves as a antagonist of $\alpha_{2A}$ (IC50 of 404 nM), $\alpha_{2B}$ (IC50 of 2140 nM) and $\alpha_{2C}$ (IC50 of 2784 nM).

Example 8

MDI Formulation 79.4 mg trifluoromethylated dihydroergotamine mesylate is dispersed in 5 mL formulation, consisting of a mixture of HFA 134a (1,1,1,2-tetrafluoroethane) and HFA 227ea (1,1,1,2,3,3,3-heptafluoropropane ranging from 0-100% HFA 227ea. Product is filled using Pamasol filling equipment into aluminum aerosol canisters through a pharmaceutically acceptable 63 µL metering valve.

Example 9

MDI Formulation with PEG 127 mg trifluoromethylated dihydroergotamine mesylate is dispersed in 8 mL formulation, consisting of a mixture of 25% HFA 134a (1,1,1,2-tetrafluoroethane) and 75% HFA 227ea (1,1,1,2,3,3,3-heptafluoropropane and containing 0.1% w/v PEG 1000 as a suspension stabilizing agent. When tested for aerosol particle size distribution using a next generation Impactor (NGI) at 60 Lmin$^{-1}$, fine particles fraction (% of emitted dose <5 µm vs. emitted dose) is anticipated to be >15%.

Example 10

MDI Formulation with Soy Lethicin 119 mg trifluoromethylated dihydroergotamine mesylate is dispersed in 5 mL formulation, consisting of a mixture of 33% HFA 134a (1,1,1,2-tetrafluoroethane) and 67% HFA 227ea (1,1,1,2,3,3,3-heptafluoropropane and containing 0.01% w/v hydrogenated soy lecithin as a suspension stabilizing agent. When tested for aerosol particle size distribution using a next generation Impactor (NGI) at 60 Lmin$^{-1}$, fine particles fraction (% of emitted dose <5 µm vs. emitted dose) is anticipated to be >15%.

Example 11

MDI Formulation with Oleic Acid 79.4 mg trifluoromethylated dihydroergotamine mesylate, dissolved in 5 mL formulation, consisting of a mixture of 33% HFA 134a (1,1,1,2-tetrafluoroethane) and 67% HFA 227ea (1,1,1,2,3,3,3-heptafluoropropane and containing 0.2% w/v oleic acid as a suspension stabilizing agent and 5% w/v ethanol. When tested for aerosol particle size distribution using a next generation Impactor (NGI) at 60 Lmin$^{-1}$, fine particles fraction (% of emitted dose <5 µm vs. emitted dose) is anticipated to be >15%.

Example 12

DPI Formulation 154 g trifluoromethylated dihydroergotamine mesylate is sandwich layered between a total of 847 g inhalation grade lactose (Respitose® SV003), and then is blended on a Turbula blender at 42 rpm for 45 minutes. The formulation is then sieved through a 125 µm aperture sieve twice and filled (13 mg fill weight) into inhalation capsules. When tested for aerosol particle size distribution using a next generation Impactor (NGI) at 60 Lmin$^{-1}$, fine particles fraction (% of emitted dose <5 µm vs. emitted dose) is anticipated to be >15%.

Example 13

DPI Formulation 77 g trifluoromethylated dihydroergotamine mesylate is sandwich layered between a total of 423 g inhalation grade lactose (Respitose® ML001), and is then blended with high shear mixing at 2000 rpm for 45 minutes. The formulation is then sieved through a 125 µm aperture sieve twice and filled (13 mg fill weight) into inhalation capsules. When tested for aerosol particle size distribution using a next generation Impactor (NGI) at 60 Lmin$^{-1}$, fine particles fraction (% of emitted dose <5 µm vs. emitted dose) is anticipated to be >15%.

Example 14

Nasal Suspension Formulation

2% w/v trifluoromethylated dihydroergotamine mesylate is suspended using high shear mixing into a formulation comprising microcrystalline cellulose (Avicel RC-591, 1.5%), dextrose (5.0%), polysorbate 80 (0.007%), glycerol (4.0%), propylene glycol (1.0%), Citric acid monohydrate (0.2%), disodium hydrogen orthophosphate, anhydrous (0.31%), phenylethyl alcohol (0.275%), benzalkonium chloride (0.02%) and water (87.69%) and is filled into borosilicate glass bottles fitted with a pharmaceutically acceptable 100 µL metering valve. When tested using standard nasal testing equipment, shot weight is with 80-120% of target and emitted dose from the spray actuator is >80%.

Example 15

Metabolism Study of 2-CF3 Dihydroergotamine

Figure 4:
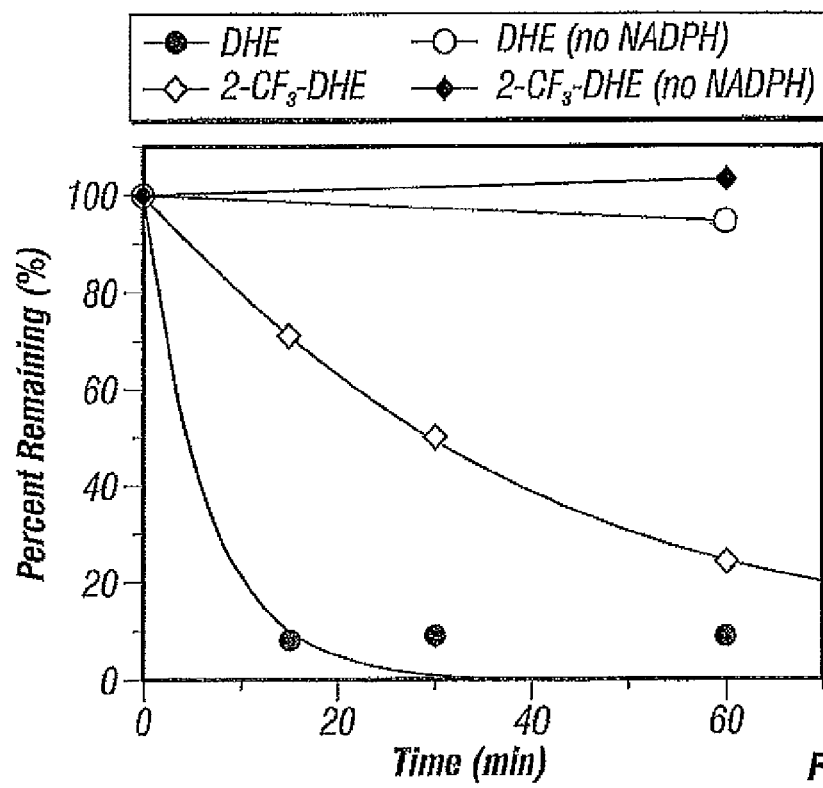
FIG. 4 illustrates that both compounds (DHE and 2-CF3-DHE) were metabolized by the human liver microsomes in the presence of NADPH with the intrinsic clearance of 2-CF3-DHE being about 85% slower than that of DHE.

Metabolism of dihydroergotamine (DHE) and 2-CF3 DHE was evaluated in human liver microsomes. DHE mesylate and 2-CF3 DHE mesylate (1 µM each) were incubated separately with human liver microsomes (0.2 mg protein/mL) in triplicate at 37° C. in 0.2 mL (final volume) incubation buffer (50 mM potassium phosphate buffer, pH 7.4, 3 mM MgCl2 and 1 mM EDTA, pH7.4) with or without cofactor, NADPH-generating system. The NADPH-generating system consisted of 1 mM NADP, pH 7.4, 5 mM glucose-6-phosphate, pH 7.4 and 1 unit/mL glucose-6-phosphate dehydrogenase. DHE was added to the incubation mixtures in water. 2-CF3-DHE was added to incubation mixtures in 50:50 (v:v) acetonitrile:water. A low level of acetonitrile in the incubation was maintained to avoid any solvent effects on enzyme activity (typically at 0.5% or lower). Reactions were initiated by the addition of the NADPH-generating system and were terminated at 0, 15, 30 and 60 minutes after initiation by the addition of 175 µL of stop reagent (acetonitrile) containing two internal standards (4'-hydroxydiclofenac-d4 and 1'-hydroxymidazolam-d4, 200 and 50 ng/mL in the final stopped incubation, respectively). The samples were then centrifuged and the supernatant fractions were analyzed by LC/MS/MS to quantify the formation of 8'-OH-DHE (metabolite) in the DHE samples and DHE and 8'-OH-DHE in the 2-CF3-DHE samples. The results (shown in FIG. 4) showed that both compounds (DHE and 2-CF3-DHE) were extensively metabolized by the human liver microsomes in the presence of NADPH. The intrinsic clearance of 2-CF3-DHE was about 85% slower than that of DHE, which is consistent with the conclusion that the 2-CF3-DHE compound is metabolically more stable than DHE.

Example 16

Genotox Studies of 2-CF3 Dihydroergotamine

Genotoxicity studies were performed to evaluate the potential mutagenic activity of 2-CF3-DHE. Studies were performed to examine the ability of 2-CF3-DHE to revert five histidine-requiring strains of *Salmonella typhimurium* in the absence and presence of a rat liver metabolizing system. Results showed no statistically significant increases in the revertant numbers when the data was analyzed at the 1% level using Dunnett's test. This is consistent with the conclusion that there was no evidence of any mutagenic activity observed with 2-CF3-DHE.

Example 17

Effects of 2-CF3 Dihydroergotamine on Coronary Arteries and Saphenous Vein

Human coronary arteries and saphenous veins were set up under isometric conditions on either small vessel wire myographs or organ baths, depending on vessel size, in order to examine the influence of the test article on the relative changes in tension. In order to assess tissue viability, the vessel segments were constricted with a high potassium solution (KPSS, 62.5 mM) three times. Vessels were then preconstricted with sumatriptan (1 µM) and endothelium-dependent vasorelaxation investigated using bradykinin (10 µM). If an artery segment failed to respond to KPSS or sumatriptan, it was not used in the next stage of the protocol. All vessels were fully relaxed at the end of the experiment using forskolin (10 µM).

Coronary arteries and small saphenous veins, having been cut into ring segments of approximately 2 mm length, were attached by 40 µm diameter wire running through the lumen of the vessel to stainless steel heads in 5 mL myograph baths containing PSS (physiological saline solution), aerated with 95% O2 and 5% CO2 and maintained at a temperature of 37° C. Changes in tension were recorded using a Danish Myotech isometric transducer. The vessel segments were allowed to equilibrate for at least 30 minutes after set up. Segments were processed through a standardization procedure of tension application, which reduces signal variability and allows for optimal tissue response to be obtained prior the pharmacological intervention. Saphenous veins which were too large to run on myograph baths were set up in an organ bath system. Vessels were treated in the same manner as the small vessels but were attached to an isometric transducer in an organ bath system. Vessels were equilibrated for at least 30 minutes after set up and then set to 10 mN (approximately 1 g) of tension.

Cumulative concentration response curves (CCRCs) were completed for vehicle control, sumatriptan (100 pM to 10 µM in half-log steps), and 2-CF3 dihydroergotamine (100 pM to 10 µM in half-log steps); each condition n=6. For the studies using coronary arteries, as shown in FIG. 5, the vehicle control displayed no change in tension during the course of the experiments. As expected, sumatripan displayed a constriction curve with an $EC_{50}$ value of 112 nM. 2-CF3-DHE (labeled CBT001/02 in FIG. 5), displayed only a very slight mean increase in tension. For the studies using saphenous veins, CCRCs were completed for each test condition in saphenous veins from 6 donors. As shown in FIG. 6, the vehicle control displayed no change in tension during the course of the experiments. 2-CF3-DHE (labeled CBT001/02 in FIG. 6), displayed a response similar to the vehicle and induced no change in tension. As expected, sumatriptan produced a constriction curve with an $EC_{50}$ value of 187 nM. Taken together, these data is consistent with conclusion that, along with other properties, having an anti-migraine agent that is a selective agonist for the $5\text{-HT}_{1D}$ receptor over the $5\text{-HT}_{1B}$ receptor will minimize the undesired excessive vasoconstriction that is seen with compounds such as sumatriptan.

Example 18

Scalable, High-Yield Synthesis of 2-CF3 Dihydroergotamine

2-CF3-DHE was synthesized using the following synthesis route:

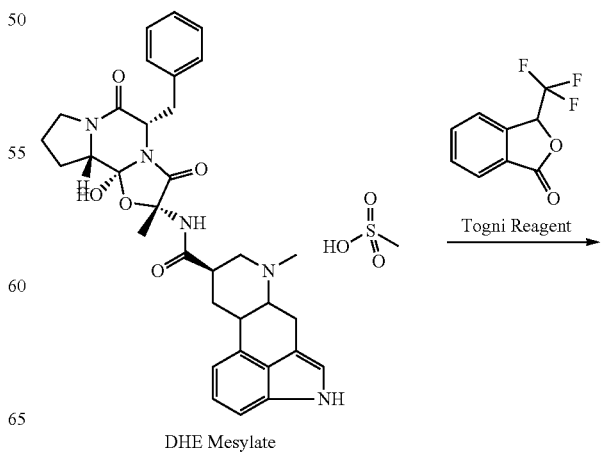

DHE Mesylate

-continued

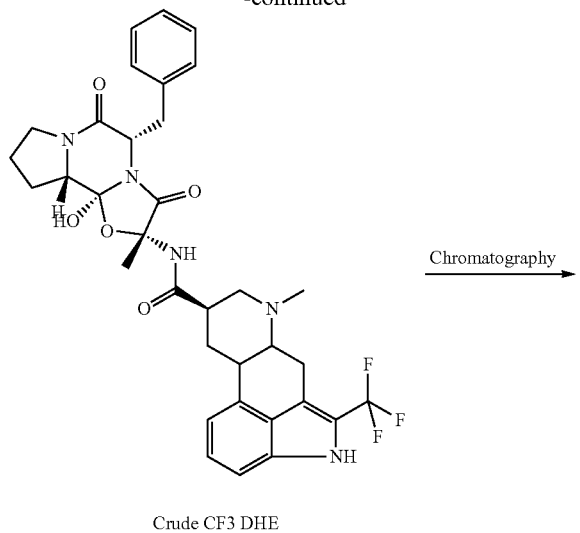

Crude CF3 DHE

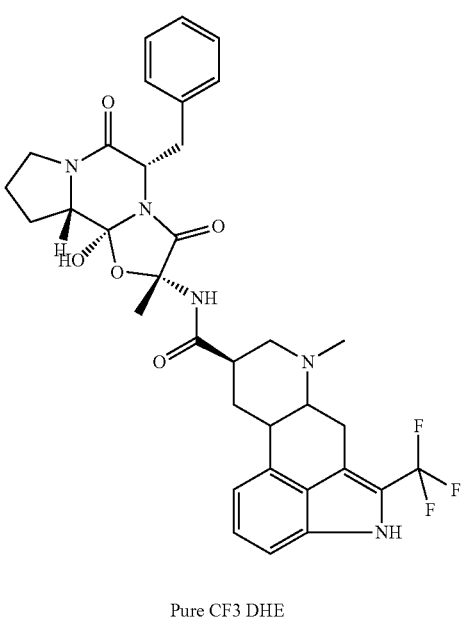

Pure CF3 DHE

DHE mesylate (80 g) and DMSO (320 mL) were charged into a 3 L 3-neck RBF equipped with an overhead stirrer, temperature probe and $N_2$ intlet/outlet. The mixture was agitated to obtain a clear orange solution. $Et_3N$ (17.22 mL, 1.05 eq.) was added to the mixture was stirred at ambient temperature for 5 minutes prior to the addition of CuOAc (0.72 g, 5 mol %). Togni's reagent (44.64 g, 1.2 eq.) dissolved in DMSO (at least 6.5 volumes) was charged into the blue mixture over 1 to 3 hours at around 20° C. The mixture was kept at 20° C. for at least 30 minutes. The mixture was then cooled to around 5° C. in an ice/water bath. EtOAc (800 mL, 10 vols) was added to the dark brown mixture. Saturated NaHCO3 solution (800 mL, 10 vols) was added into the mixture in 30 minutes in a rate to keep the temperature below 20° C. The mixture was stirred for 30 minutes and then the phases were separated in a 2 L separatory funnel. The organic layer was washed with saturated 1:1 NaHCO3 solution/water (800 mL, 10 vols) and 10% brine solution (800 mL, 10 vols). The remaining organic solution was then subjected to preparative chromatography for purification (normal phase with amino stationary phase and heptane/ethanol (80/20) as eluent). The collected fraction showed a purity of 99.2% with 95% yield. The fraction containing the product were then concentrated to dryness to afford final API product.

What is claimed is:

1. A method of treating migraine in a subject comprising administering to the subject in need thereof a therapeutically effective amount of a compound having the structure:

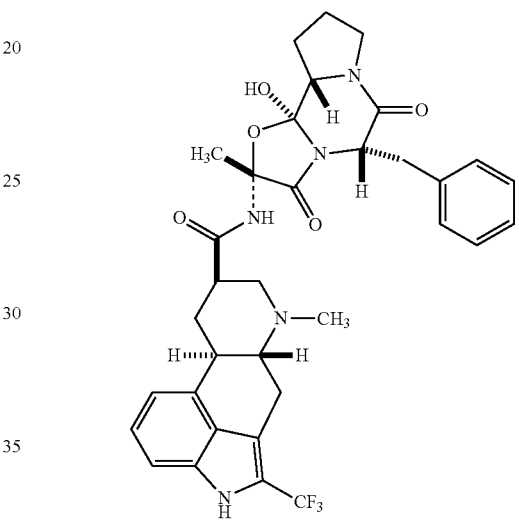

or a salt thereof, wherein the route of administration is selected from the group consisting of oral administration, parenteral administration, topical administration, transdermal administration, nasal administration and oral inhalation.

2. The method of claim 1, wherein the route of administration is oral and the compound or the salt thereof is formulated into a suitable preparation selected from the group consisting of solutions, suspensions, tablets, dispersible tablets, pills, capsules, powders, sustained release formulations and elixirs.

3. The method of claim 1, wherein the route of administration is oral inhalation and the compound or the salt thereof is formulated into a suitable preparation for delivery via a nebulizer, a pressurized metered dose inhaler or a dry powder inhaler.

4. The method of claim 1, wherein the compound is administered at least once daily.

5. The method of claim 1, wherein the compound is administered in combination with one or more other active ingredients.

6. A method of treating a symptom of ALS in a subject comprising administering to the subject in need thereof a therapeutically effective amount of a compound having the structure:

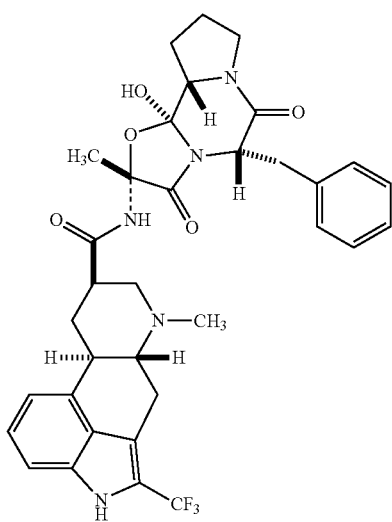

or a salt thereof.

7. The method of claim 6, wherein the compound or the salt thereof is administered with a pharmaceutically acceptable vehicle.

8. The method of claim 6, wherein the route of administration is selected from the group consisting of oral administration, parenteral administration, topical administration, transdermal administration, nasal inhalation and oral inhalation.

9. The method of claim 8, wherein the route of administration is oral and the compound or the salt thereof is formulated into a suitable preparation selected from the group consisting of solutions, suspensions, tablets, dispersible tablets, pills, capsules, powders, sustained release formulations and elixirs.

10. The method of claim 8, wherein the route of administration is oral inhalation and the compound or the salt thereof is formulated into a suitable preparation for delivery via a nebulizer, a pressurized metered dose inhaler or a dry powder inhaler.

11. The method of claim 6, wherein the compound is administered in combination with one or more other active ingredients.

\* \* \* \* \*